United States Patent
Kelsoe et al.

(10) Patent No.: US 11,512,353 B2
(45) Date of Patent: Nov. 29, 2022

(54) METHOD TO PREDICT RESPONSE TO NEUROPSYCHIATRIC DRUGS USING VARIATION IN THE SEROTONIN 7 RECEPTOR (HTR7) GENE

(71) Applicant: The Regents of the University of California, Oakland, CA (US)

(72) Inventors: John Kelsoe, Del Mar, CA (US); Yabin Wei, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 142 days.

(21) Appl. No.: 16/678,855

(22) Filed: Nov. 8, 2019

(65) Prior Publication Data
US 2020/0149109 A1    May 14, 2020

Related U.S. Application Data

(60) Provisional application No. 62/757,686, filed on Nov. 8, 2018.

(51) Int. Cl.
| | | |
|---|---|---|
| *C12Q 1/6883* | (2018.01) | |
| *C12Q 1/6827* | (2018.01) | |
| *G16H 50/30* | (2018.01) | |
| *G16B 20/20* | (2019.01) | |

(52) U.S. Cl.
CPC ......... *C12Q 1/6883* (2013.01); *C12Q 1/6827* (2013.01); *G16B 20/20* (2019.02); *G16H 50/30* (2018.01); *C12Q 2600/112* (2013.01); *C12Q 2600/118* (2013.01); *C12Q 2600/156* (2013.01)

(58) Field of Classification Search
None
See application file for complete search history.

(56) References Cited

PUBLICATIONS

Syvanen (Nature Reviews Genetics Dec. 2001 vol. 2 pp. 930-942).*
Cocchi (BMC Psychiatry 2016 16:106 pp. 1-12).*
Erdmann (Molecular Psychiatry 1996 vol. 1 pp. 392-397).*
Helsmoortel (Am J Med Genet Part B 171B:1049-1056 Jul. 6, 2016).*
Ballaz. S.J. et al. (Jun. 29, 2007, e-published Jun. 1, 2007). "Analysis of 5-HT6 and 5-HT7 receptor gene expression in rats showing differences in novelty-seeking behavior," *Neuroscience* 147(2):428-438.
Guscott, M. et al. (Mar. 2005). "Genetic knockout and pharmacological blockade studies of the 5-HT7 receptor suggest therapeutic potential in depression," *Neuropharmacology* 48(4):492-502.
Hannon, J. et al. (Dec. 16, 2008, e-published Mar. 25, 2008). "Molecular biology of 5-HT receptors," *Behav Brain Res* 195(1):198-213.
Keers, R. et al. (2010). "Gender differences in antidepressant drug response," *Int Rev Psychiatry* 22(5):485-500.
Kim, J.H. et al. (Sep. 2014, e-published Jul. 28, 2014). "Association between HTR7 genetic polymorphisms and alcohol dependence, using the alcohol use disorders identification test (AUDIT)," *Alcohol Clin Exp Res* 38(9):2354-2361.
Martenyi, F. et al. (Jun. 2001). "Gender differences in the efficacy of fluoxetine and maprotiline in depressed patients: a double-blind trial of antidepressants with serotonergic or norepinephrinergic reuptake inhibition profile," *Eur Neuropsychopharmacol* 11(3):227-232.
Mowry, B.J. et al. (Dec. 4, 2000). "Second stage of a genome scan of schizophrenia: study of five positive regions in an expanded sample," *Am J Med Genet* 96(6):864-869.
Uher, R. et al. (Aug. 2009, e-published Apr. 14, 2009). Genetic predictors of response to antidepressants in the GENDEP project, *Pharmacogenomics J* 9(4):225-233.
Wei, Y.B. et al. (Jan. 1, 2016, e-published Sep. 16, 2015). "hTERT genetic variation in depression," *J Affect Disord* 189:62-69.

* cited by examiner

*Primary Examiner* — Amanda Haney
(74) *Attorney, Agent, or Firm* — Mintz, Levin, Cohn, Ferris, Glovsky and Popeo, P.C.

(57) ABSTRACT

Provided herein are, inter alia, methods whereby response to psychotropic drugs can be predicted, methods of treating neuropsychiatric disorders, and methods of detecting a single nucleotide polymorphism (SNP) relating to treating neuropsychiatric disorders.

10 Claims, 4 Drawing Sheets
Specification includes a Sequence Listing.

| Biotin probe spanning rs7905226-T/G site | T | T | T | T | G | G | G | G |
| --- | --- | --- | --- | --- | --- | --- | --- | --- |
| Nuclear extract | - | + | + | + | - | + | + | + |
| Specific competitor | - | - | + | - | - | - | + | - |
| Anti-CEBPB | - | - | - | + | - | - | - | + |

SEQUENCE LISTING

```
<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Lab-made

<400> SEQUENCE: 1
taagcaaagc ttaattcccc ttggtatcca aaccc                              35

<210> SEQ ID NO 2
<211> LENGTH: 36
<212> TYPE: DNA
<213> ORGANISM: Artificial Sequence
<220> FEATURE:
<223> OTHER INFORMATION: Lab-made

<400> SEQUENCE: 2
taagcagcta gcatattgct ttgtggccta ggtatt                             36

<210> SEQ ID NO 3
<211> LENGTH: 34
<212> TYPE: DNA
<213> ORGANISM: Artificial Sequence
<220> FEATURE:
<223> OTHER INFORMATION: Lab-made

<400> SEQUENCE: 3
gagtcagagg aagagttgaa tataatacct aggc                               34

<210> SEQ ID NO 4
<211> LENGTH: 34
<212> TYPE: DNA
<213> ORGANISM: Artificial Sequence
<220> FEATURE:
<223> OTHER INFORMATION: Lab-made

<400> SEQUENCE: 4
gagtcagagg aagagtggaa tataatacct aggc                               34
```

METHOD TO PREDICT RESPONSE TO NEUROPSYCHIATRIC DRUGS USING VARIATION IN THE SEROTONIN 7 RECEPTOR (HTR7) GENE

CROSS REFERENCE TO RELATED APPLICATIONS

This application claims priority to U.S. Provisional Application No. 62/757,686, filed Nov. 8, 2018, which is hereby incorporated by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048537-617001US_SEQUENCE_LISTING_ST25.txt created on Nov. 4, 2019, 1,056 bytes, machine format IBM-PC, MS Windows operating system, is hereby incorporated by reference.

BACKGROUND

Background. Serotonin (5-HT) is a monoamine neurotransmitter with a broad range of physiological functions including circadian rhythms, body temperature, food intake, sleep, mood, cardiovascular function and endocrine regulation. These effects are mediated by a large number of 5-HT receptors, comprising seven main families (HTR1 to HTR7) and at least 14 subtypes [1,2]. HTR7 is the most recently discovered 5-HT receptor, which is a G-protein-coupled receptor that links to adenylate cyclase and transduces signals mainly through the cAMP pathway [3,4]. HTR7 has been shown to express abundantly both at peripheral tissues like smooth muscle and intestine and in brain regions including forebrain, hippocampus, hypothalamus, brainstem and cerebellum [3, 5-7]. A growing body of evidence have indicated HTR7 plays a role in the pathophysiology of psychiatric disorders. Genome-wide genetic studies have suggested a relationship between HTR7 genetic polymorphism and schizophrenia and decreased HTR7 expression were reported in postmortem brain of schizophrenic patients [8-10]. Genetic variation in HTR7 has also been shown to predispose to the development of alcohol dependence [11, 12]. Preclinical studies implied HTR7 influenced behaviors in rodents that mimic obsessive-compulsive disorder and substance abuse [13,14]. Much attention has been devoted to the possible role of HTR7 in depression. HTR7 knock-out mice or pharmacological blockade of the HTR7 showed an antidepressant-like behavior [15-18]. In addition, blockade HTR7 by SB-269970 was found to potentiate the effects of selective serotonin reuptake inhibitors (SSRI) and norepinephrine reuptake inhibitors (NARI) [16]. HTR7 may in part interact with the action of antidepressants. Several antidepressants both tricyclics and SSRI, can induce c-fos expression in a fashion that is similar to HTR7 activation while chronic treatment by fluoxetine downregulates HTR7 expression [19,20]. Indeed, several antidepressants and antipsychotic drugs with clinically established antidepressant effect showed high affinity to HTR7, such as amitriptyline, amoxapine, amisulpride, clozapine, aripiprazole, lurasidone, risperidone and perospirone [21-24]. Thus, the above evidence suggests HTR7 may serve as a potential candidate for therapeutic targets of depression. However, studies of genetic polymorphisms in HTR7 in clinical depression have been limited and whether those genetic polymorphisms can predict treatment outcome remains elusive.

Bipolar disorder (BD) is a complex and chronic psychiatric condition affecting 1-2% of the population, which characterized as shifts in mood between manic and depressive states [25]. Lithium is the first-line mood stabilizer in treating BD however less than half of the BD patients achieve optimal response to lithium [26]. Although the mania is the most dramatic manifestation of BD, in reality patients spend most of their time depressed when ill [27]. Treating bipolar depression remains a considerable clinical challenge. Although some reports showed SSRI may increase the risk of a manic switch, the clinical use of SSRI in BD is still common and many studies showed it is safe and effective [28,29]. Several large-scale genome-wide association studies have examined the association between genetic markers and antidepressant response, however only a limited number of SNPs in HTR7 have been covered [30-32].

Predicting antidepressant and antipsychotic response has been a clinical challenge for the treatment of neuropsychiatric disorders. Patients commonly have to undergo trials of multiple medications before a regimen is found that is optimal for them. During this period, they continue to suffer and may be at risk for suicide. There remains a need for solutions to this and other issues in the art.

BRIEF SUMMARY

The present disclosure provides methods whereby response to psychotropic drugs can be predicted, methods of treating neuropsychiatric disorders, and methods of detecting a single nucleotide polymorphism (SNP) relating to treating neuropsychiatric disorders.

In an aspect, a method of determining whether a neuroactive drug is suitable for treating a subject undergoing treatment for a neuropsychiatric disorder is provided. The method includes determining a rs7905446 single nucleotide polymorphism (SNP) in the subject, wherein the presence of a TT genotype indicates that a selective serotonin reuptake inhibitor (SSRI) or noradrenergic reuptake inhibitor (NARI) is unsuitable for treating the subject; and, wherein the presence of a GG or GT genotype indicates that a SSRI or noradrenergic reuptake inhibitor (NARI) is suitable for treating the subject.

In another aspect, a method of determining whether a neuroactive drug is suitable for treating a subject undergoing treatment for a neuropsychiatric disorder is provided. The method includes determining a rs7905446 single nucleotide polymorphism (SNP) in the subject, wherein the presence of a TT genotype indicates that amitriptyline, amoxapine, amisulpride, clozapine, aripiprazole, lurasidone, risperidone or perospirone is unsuitable for treating the subject, and wherein the presence of the GG or GT genotype indicates that amitriptyline, amoxapine, amisulpride, clozapine, aripiprazole, lurasidone, risperidone or perospirone is suitable for treating the subject.

In an aspect is provided a method of treating a subject for a neuropsychiatric disorder. The method includes determining a rs7905446 single nucleotide polymorphism (SNP) in the subject; and administering an effective amount of a SSRI or NARI to the subject if a GG or GT genotype is present; or, administering an effective amount of a neuroactive compound other than SSRI or NARI to the subject if a TT genotype is present.

In another aspect is provided a method of treating a subject for a neuropsychiatric disorder. The method includes: determining a rs7905446 single nucleotide polymorphism (SNP) in the subject; and administering an effective amount of amitriptyline, amoxapine, amisulpride, clozapine, aripiprazole, lurasidone, risperidone or perospirone to the subject if a gg genotype is present; or, administering an effective amount of a neuroactive compound other than amitriptyline, amoxapine, amisulpride, clozapine, aripiprazole, lurasidone, risperidone or perospirone to the subject if a TT genotype is present.

In an aspect is provided, a method of treating a subject for a neuropsychiatric disorder, the subject undergoing treatment with a SSRI or NARI. The method includes: determining a rs7905446 single nucleotide polymorphism (SNP) in the subject; and continuing administration of an effective amount of a SSRI or NARI to the subject if a GG or GT genotype is present; or, discontinuing administration of a SSRI or NARI to the subject if a TT genotype is present and administering an effective amount of a neuroactive compound other than a SSRI or NARI.

In an aspect, a method of treating a subject for a neuropsychiatric disorder is provided. The method includes: determining the rs7905446 single nucleotide polymorphism (SNP) in the subject; and continuing administration of amitriptyline, amoxapine, amisulpride, clozapine, aripiprazole, lurasidone, risperidone or perospirone to the subject if a GG or GT genotype is present; or, discontinuing administration of amitriptyline, amoxapine, amisulpride, clozapine, aripiprazole, lurasidone, risperidone or perospirone to the subject if a TT genotype is present and administering an effective amount of a neuroactive compound other than amitriptyline, amoxapine, amisulpride, clozapine, aripiprazole, lurasidone, risperidone or perospirone.

In another aspect, a method of detecting a single nucleotide polymorphism (SNP) in a subject is provided. The method includes detecting in a biological sample from the subject the presence of a rs7905446 single nucleotide polymorphism (SNP).

In another aspect, a kit for predicting the suitability of a neuroactive compound in a subject with a neuropsychiatric disorder is provided. The kit includes at least one nucleic acid probe or primer for detecting a rs7905446 single nucleotide polymorphism (SNP).

DETAILED DESCRIPTION

I. Definitions

Figure 1:
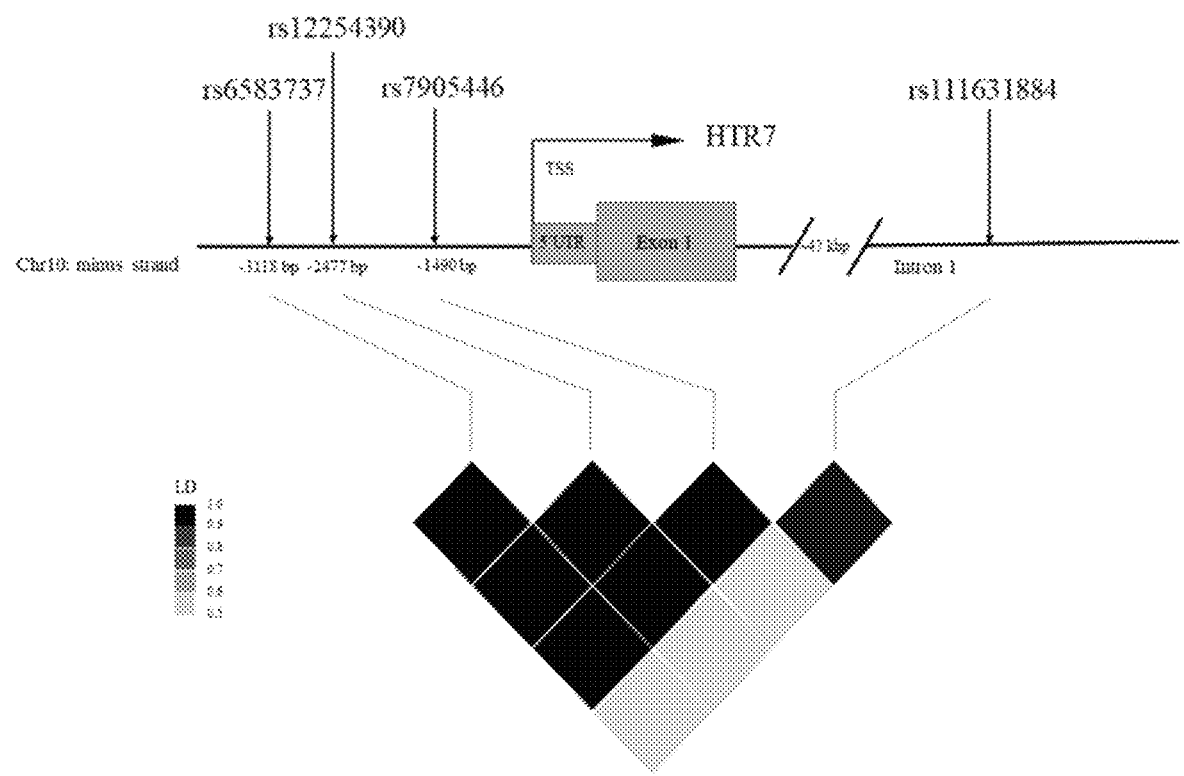
FIG. 1. Position of top SNPs in paroxetine group which showed high linkage with each other. Two SNPs in 5' upstream region (rs6583737, rs12254390), one SNP in the proximal promoter (rs7905446) and one SNP in the first intron (rs111631884) of HTR7 gene showed significant association with response to paroxetine. TSS: transcription start site.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Biological sample" refers to any biological sample taken from a subject. Biological samples include blood, plasma, serum, tumors, tissue, cells, cheek swabs, skin biopsy, orally obtained cells and the like. Biological samples can be taken from a subject by methods known in the art, and can be analyzed by methods known in the art.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

An amino acid residue in a protein "corresponds" to a given residue when it occupies the same essential structural position within the protein as the given residue.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein"

refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, *Scientific American,* 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and -anomeric sugar-phosphate, back bone modified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.,* 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "genotype" is used herein according to its plain ordinary meaning within Genetics and refers to part of the genetic makeup of a cell, individual, or organism. For example, genotype refers to alleles or variant forms of a gene that are carried by an organism. Genotype may refer to an individual's genotype with regard to a particular gene of interest. For example, genotype may refer to a single-nucleotide polymorphism.

The terms "single-nucleotide polymorphism" or "SNP" are used herein according to its plain ordinary meaning within Genetics and refers to a substitution of a single nucleotide that occurs at a specific position in the genome. For example, SNPs may fall within coding sequences of genes, non-coding regions of genes, or in the intergenic regions (regions between genes). SNPs within a coding sequence may not change the amino acid sequence of the protein that is produced, due to degeneracy of the genetic code. SNPs in the coding region may be of two types: synonymous and nonsynonymous SNPs. Synonymous SNPs do not affect the protein sequence, while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of noncoding RNA.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "genetic variant," in the context of a particular gene, refers a gene with a variant (e.g., non-standard or abnormal) nucleic acid sequence. The gene includes coding and non-coding sequences, such as regulatory regions. Genetic variants include mutations and polymorphic sequences. Thus, the genetic variant may affect the expression or activity of the gene or gene product. The genetic variant may be an insertion of one or more nucleotides, deletion of one or more nucleotides, or a substitution of one or more nucleotides. A single nucleotide polymorphism (SNP) is an example of a genetic variant.

The terms "HTR7 gene", "serotonin 7 receptor gene", "5-HT7" or the like, as used herein refer to the any of the recombinant or naturally-occurring forms of the 5-hydroxytryptamine receptor 7 gene or variants or homologs thereof that code for a 5-hydroxytryptamine receptor 7 polypeptide capable of maintaining the activity of the 5-hydroxytryptamine receptor 7 polypeptide (e.g., within at least 50%, 80%, 90%, 95%, 96%, 97%, 98%, 99% or 100% activity compared to 5-hydroxytryptamine receptor 7 polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring 5-hydroxytryptamine receptor 7 gene. In embodiments, the 5-hydroxytryptamine receptor 7 gene is substantially identical to the nucleic acid sequence identified by UniProtKB No. P34969 or a variant or homolog having substantial identity thereto. In embodiments, the 5-hydroxytryptamine receptor 7 gene is substantially identical to the nucleic acid sequence identified by Entrez Gene ID 3363.

The terms "CEPBP gene", "CCAAT/enhancer-binding protein beta", or the like, as used herein refer to the any of the recombinant or naturally-occurring forms of the CCAAT/enhancer-binding protein beta or variants or homologs thereof that code for a CCAAT/enhancer-binding protein beta polypeptide capable of maintaining the activity of the CCAAT/enhancer-binding protein beta polypeptide (e.g., within at least 50%, 80%, 90%, 95%, 96%, 97%, 98%, 99% or 100% activity compared to CCAAT/enhancer-binding protein beta polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring CCAAT/enhancer-binding protein beta gene. In embodiments, the CCAAT/enhancer-binding protein beta gene is substantially identical to the nucleic acid sequence identified by UniProtKB No. P17676 or a variant or homolog having substantial identity thereto. In embodiments, the CCAAT/enhancer-binding protein beta gene is substantially identical to the nucleic acid sequence identified by Entrez Gene ID 1051.

The term "adenylate cyclase" or "adenylate cyclase protein" as provided herein includes any of the recombinant or naturally-occurring forms of adenylyl cyclase, also known as ATP pyrophosphate-lyase, or variants or homologs thereof that maintain adenylate cyclase activity (e.g. within at least 50%, 80%, 90%, 95%, 96%, 97%, 98%, 99% or 100% activity compared to adenylate cyclase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring adenylate cyclase polypeptide. In embodiments, adenylate cyclase is the protein as identified by the Unitprot sequence reference: Q08828, homolog or functional fragment thereof. In embodiments, adenylate cyclase is the protein as identified by the NCBI sequence reference GI: 516263, homolog or functional fragment thereof. In embodiments, adenylate cyclase is the protein as identified by the NCBI sequence reference GI: 4104226, homolog or functional fragment thereof.

The term "5-hydroxytryptamine receptor 7" or "5-hydroxytryptamine receptor 7 protein" as provided herein includes any of the recombinant or naturally-occurring forms of 5-hydroxytryptamine receptor 7 (HTR7), also known as 5-HT-7, 5-HT7, or variants or homologs thereof that maintain HTR7 activity (e.g. within at least 50%, 80%, 90%, 95%, 96%, 97%, 98%, 99% or 100% activity compared to HTR7). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HTR7 polypeptide. In embodiments, HTR7 is the protein as identified by the Unitprot sequence reference: P34969, homolog or functional fragment thereof. In embodiments, HTR7 is the protein as identified by the NCBI sequence reference GI: 8488960, homolog or functional fragment thereof.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

The terms "selective serotonin reuptake inhibitor" or "SSRI" as used herein refer to a class of drugs that modulate levels of serotonin, a neurotransmitter, in the brain. SSRIs are typically used as antidepressants in the treatment of depression (e.g., depression, major depression) and anxiety disorders. The specific action of SSRIs is unknown but they may increase the extracellular level of serotonin by limiting reuptake of serotonin. Therefore, more serotonin is available to improve transmission of messages between neurons. SSRIs are called selective because they mainly affect serotonin, not other neurotransmitters. Non-limiting examples of SSRIs include citalopram, escitalopram, fluoxetine, fluvoxamine, paroxetine, and sertraline.

The terms "noradrenergic reuptake inhibitor" or NARI" as used herein refer to a class of drugs that act as reuptake inhibitors for the neurotransmitters norepinephrine (noradrenaline) and epinephrine (adrenaline). For example, a NARI functions by blocking the action of the norepinephrine transporter (NET). This may lead to increased extracellular concentrations of norepinephrine and epinephrine, therefore increasing adrenergic neurotransmission. Non-limiting examples of NARIs include desipramine, nortyptiline, bupropion, mirtazapine, maprotiline or atomoxetine.

Table 1 shows the names and structures of non-liming examples of neuroactive drugs.

TABLE 1

| Names and structures of neuroactive drugs | |
|---|---|
| Name | Structure |
| Citalopram Citalopram is a racemic mixture of the two stereoisomers (R)-(−)-citalopram (top) and (S)-(+)-citalopram (bottom) | 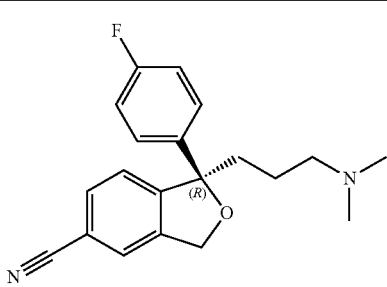 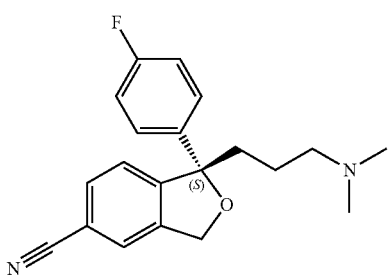 |

TABLE 1-continued

Names and structures of neuroactive drugs

| Name | Structure |
|---|---|
| Escitalopram | 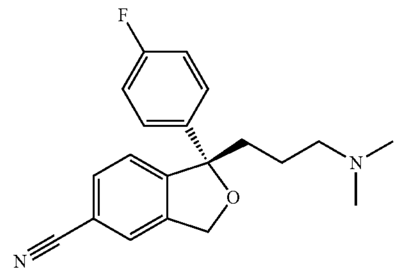 [SMILES: CN(C)CCC[C@@]1(c2ccc(F)cc2)OCc2cc(C#N)ccc21] |
| Paroxetine | 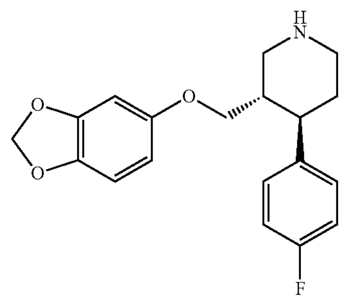 [SMILES: Fc1ccc([C@@H]2CCNC[C@H]2COc2ccc3c(c2)OCO3)cc1] |
| Fluoxetine | 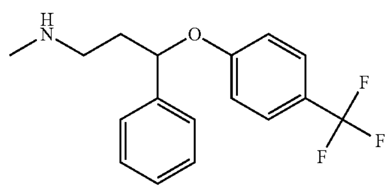 [SMILES: CNCCC(Oc1ccc(C(F)(F)F)cc1)c1ccccc1] |
| Fluvoxamine | 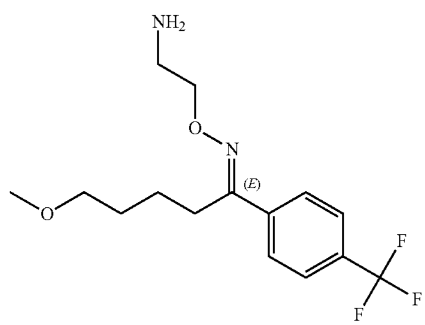 [SMILES: COCCCC/C(=N\OCCN)c1ccc(C(F)(F)F)cc1] |
| Sertraline | 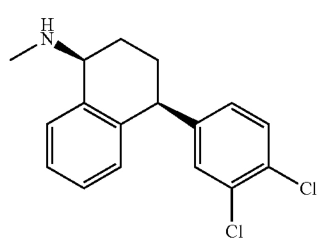 [SMILES: CN[C@H]1CC[C@@H](c2ccc(Cl)c(Cl)c2)c2ccccc21] |
| Amisulpride | 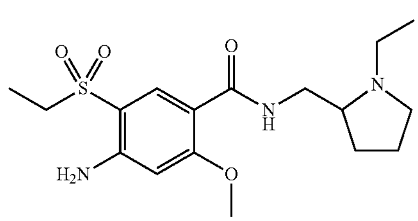 [SMILES: CCN1CCCC1CNC(=O)c1cc(S(=O)(=O)CC)c(N)cc1OC] |

TABLE 1-continued

Names and structures of neuroactive drugs

| Name | Structure |
| --- | --- |
| Amitriptyline | 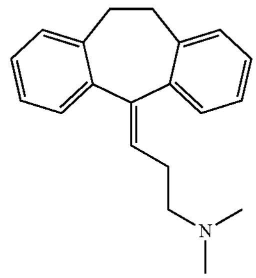 [SMILES: CN(C)CCC=C1c2ccccc2CCc2ccccc21] |
| Amoxapine | 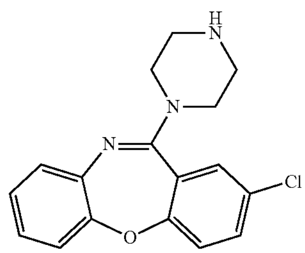 [SMILES: Clc1ccc2c(c1)C(N1CCNCC1)=Nc1ccccc1O2] |
| Clozapine | 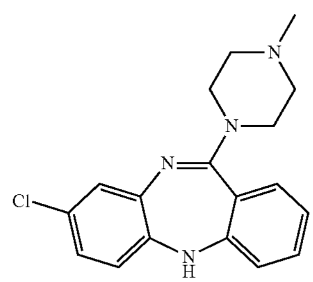 [SMILES: CN1CCN(C2=Nc3cc(Cl)ccc3Nc3ccccc32)CC1] |
| Aripiprazole | 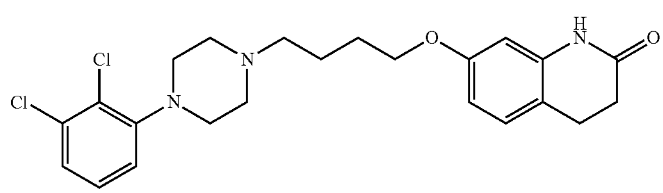 [SMILES: O=C1CCc2ccc(OCCCCN3CCN(c4cccc(Cl)c4Cl)CC3)cc2N1] |
| Lurasidone | 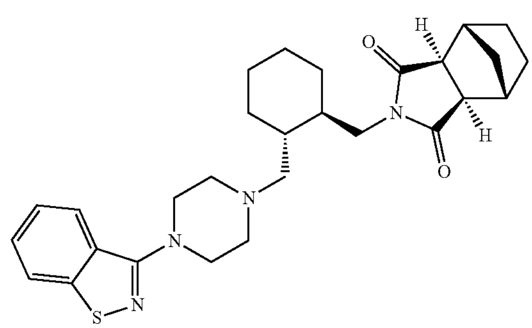 [SMILES: O=C1[C@@H]2[C@H]3CC[C@H](C3)[C@@H]2C(=O)N1C[C@@H]1CCCC[C@H]1CN1CCN(c2nsc3ccccc23)CC1] |
| Risperidone | 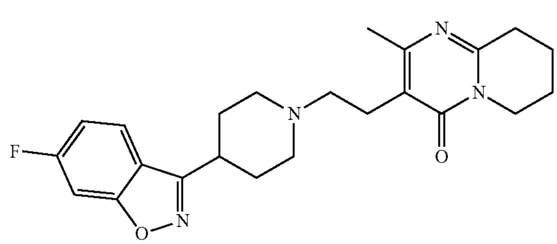 [SMILES: Cc1nc2n(c(=O)c1CCN1CCC(c3noc4cc(F)ccc34)CC1)CCCC2] |

TABLE 1-continued

Names and structures of neuroactive drugs

| Name | Structure |
| --- | --- |
| Perospirone | 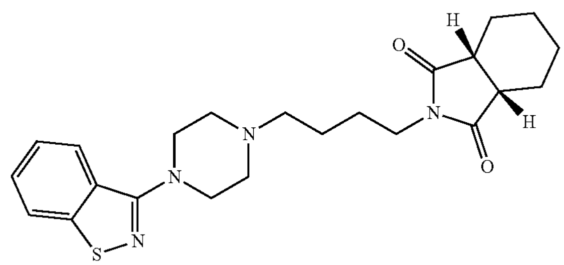 [SMILES: O=C1[C@H]2CCCC[C@H]2C(=O)N1CCCCN1CCN(c2nsc3ccccc23)CC1] |
| Desipramine | 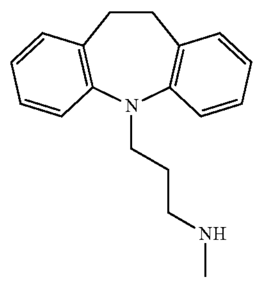 [SMILES: CNCCCN1c2ccccc2CCc2ccccc21] |
| Nortyptiline | 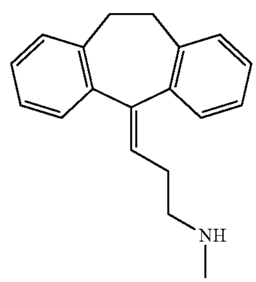 [SMILES: CNCCC=C1c2ccccc2CCc2ccccc21] |
| Bupropion | 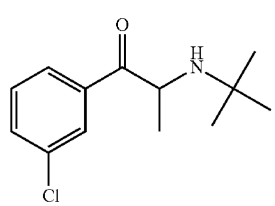 [SMILES: CC(NC(C)(C)C)C(=O)c1cccc(Cl)c1] |
| Mirtazapine | 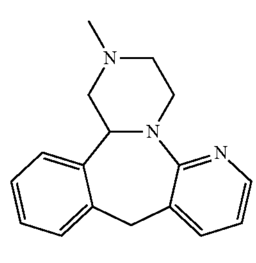 [SMILES: CN1CCN2c3ncccc3Cc3ccccc3C2C1] |

TABLE 1-continued

Names and structures of neuroactive drugs

| Name | Structure |
|------|-----------|
| Maprotiline | 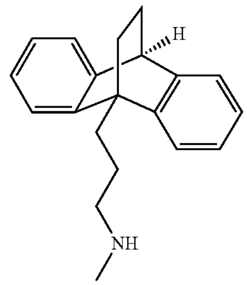 |
| Atomoxetine | 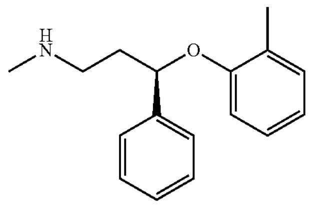 [SMILES: CNCC[C@@H](Oc1ccccc1C)c1ccccc1] |

To determine efficacy of treatment in psychiatric disorders (e.g., depression, major depression) questionnaires (e.g., self-reporting questionnaires) may be used. Non-limiting examples of questionnaires useful for assessing treatment efficacy in psychiatric disorders (e.g., depression, major depression) include the Hamilton Rating Scale for Depression; the Hamilton Rating Scale for Depression 17 item (HAMD$_{17}$ or HAMD-17); the 21 item HAMD (HAMD$_{21}$); the 24 item HAMD (HAMD$_{24}$); the Quick Inventory of Depressive Symptoms (QIDS); the Mood and Symptom Questionnaire subscale scores for Anxious Arousal, Anhedonic Depression, and General Distress; the Montgomery-Asberg Depression Scale (MADRS); the Beck Depression Inventory; the Clinical Global Impressions (GCI) scale); the Snaith-Hamilton Pleasure Scale (SHAPS). Questionnaires may be completed prior to, during, and following treatment, and changes in the scores may be used to determine treatment efficacy.

Treatment may result in a reduction of symptoms (e.g., a response) or in remission. In embodiments, a reduction in symptoms is referred to as a response. In embodiments, a response is a 50% or greater decrease in symptoms. A response (e.g., a 50% or greater decrease in symptoms) to treatment may be determined by measuring (e.g., quantifying) a change in a score as described herein, including embodiments thereof, on a questionnaire as described herein, including embodiments thereof. The treatment may refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of decline; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease.

As used herein, "neuroactive drug", "neuroactive compound", or "neuroactive agent" refers to compounds that may have an effect on behavioral actions, neuron excitability, and/or neurochemical interactions. For example, neuroactive drugs may affect central nervous system signaling pathways. Neuroactive drugs may modulate levels of neurotransmitters or interact with neurotransmitter receptors. Neuroactive drugs include but are not limited to SSRIs.

The term "neuropsychiatric disorder" as used herein refers to disorders attributable to diseases of the nervous system. A neuropsychiatric disorder may concern both neurology and psychiatry, and may affect cognition and/or behavior. Non-limiting examples of neuropsychiatric disorders include acute stress disorder, antisocial behavior, agoraphobia, Asperger syndrome, avoidant personality disorder, attention deficit/hyperactivity disorder, anxiety, body dysmorphic disorder, brief psychotic disorder, catatonic schizophrenia, schizophrenia, cognitive disorder, catalepsy, cotard delusion, derealization, dissociative identity disorder, depression, postpartum depression, personality disorders, eating disorders, epilepsy, grandiose delusions, factitious disorder, hallucinogen-related disorder, histrionic personality disorder, hysteria, imposter syndrome, addiction, migraine headaches, manic episode, narcissistic personality disorder, psychosis, uncontrolled anger, palsies, cognitive deficit disorders, attention deficit disorders, seizures, autism spectrum disorder, bipolar disorder, impulse control, dissociative disorder, panic disorder, obsessive-compulsive disorder, posttraumatic stress disorder, schizophrenia, sleep disorders, somatic symptom disorder, and specific learning disorder.

II. Methods of Use

Provided herein are, inter alia, methods for predicting whether a subject will respond to treatment with a neuropsychiatric disease by detecting variations in the serotonin 7 receptor gene and methods for treating the subject.

In one aspect is provided a method of determining whether a neuroactive drug is suitable for treating a subject undergoing treatment for a neuropsychiatric disorder. The method includes determining a rs7905446 single nucleotide polymorphism (SNP) in the subject, wherein the presence of a TT genotype indicates that a selective serotonin reuptake inhibitor (SSRI) or noradrenergic reuptake inhibitor (NARI) is unsuitable for treating the subject; and, wherein the presence of a GG or GT genotype indicates that a SSRI or noradrenergic reuptake inhibitor (NARI) is suitable for treating the subject.

In an aspect is provided a method of determining whether a neuroactive drug is suitable for treating a subject undergoing treatment for a neuropsychiatric disorder. The method includes determining a rs7905446 single nucleotide polymorphism (SNP) in the subject, wherein the presence of a TT genotype indicates that amitriptyline, amoxapine, amisulpride, clozapine, aripiprazole, lurasidone, risperidone or perospirone is unsuitable for treating the subject, and wherein the presence of the GG or GT genotype indicates that amitriptyline, amoxapine, amisulpride, clozapine, aripiprazole, lurasidone, risperidone or perospirone is suitable for treating the subject. Thus, in embodiments the presence of a TT genotype indicates that amitriptyline is unsuitable for treating the subject. In embodiments the presence of a TT genotype indicates that amoxapine is unsuitable for treating the subject. In embodiments the presence of a TT genotype indicates that amisulpride is unsuitable for treating the subject. In embodiments the presence of a TT genotype indicates that clozapine is unsuitable for treating the subject. In embodiments the presence of a TT genotype indicates that aripiprazole is unsuitable for treating the subject. In embodiments the presence of a TT genotype indicates that lurasidone is unsuitable for treating the subject. In embodiments the presence of a TT genotype indicates that risperidone is unsuitable for treating the subject. In embodiments the presence of a TT genotype indicates that perospirone is unsuitable for treating the subject. In embodiments the presence of a TT genotype indicates that amitriptyline, amoxapine, amisulpride, clozapine, aripiprazole, lurasidone, risperidone or perospirone is unsuitable for treating the subject. In embodiments the presence of the GG genotype indicates that amitriptyline is suitable for treating the subject. In embodiments the presence of the GG genotype indicates that amoxapine is suitable for treating the subject. In embodiments the presence of the GG genotype indicates that amisulpride is suitable for treating the subject. In embodiments the presence of the GG genotype indicates that clozapine is suitable for treating the subject. In embodiments the presence of the GG genotype indicates that aripiprazole is suitable for treating the subject. In embodiments the presence of the GG genotype indicates that lurasidone is suitable for treating the subject. In embodiments the presence of the GG genotype indicates that risperidone is suitable for treating the subject. In embodiments the presence of the GG genotype indicates that perospirone is suitable for treating the subject. In embodiments the presence of the GG genotype indicates that amitriptyline, amoxapine, amisulpride, clozapine, aripiprazole, lurasidone, risperidone or perospirone is suitable for treating the subject. In embodiments, the presence of the GT genotype indicates that amitriptyline is suitable for treating the subject. In embodiments, the presence of the GT genotype indicates that amoxapine is suitable for treating the subject. In embodiments, the presence of the GT genotype indicates that amisulpride is suitable for treating the subject. In embodiments, the presence of the GT genotype indicates that clozapine is suitable for treating the subject. In embodiments, the presence of the GT genotype indicates that aripiprazole is suitable for treating the subject. In embodiments, the presence of the GT genotype indicates that lurasidone is suitable for treating the subject. In embodiments, the presence of the GT genotype indicates that risperidone is suitable for treating the subject. In embodiments, the presence of the GT genotype indicates that perospirone is suitable for treating the subject. In embodiments, the presence of the GT genotype indicates that amitriptyline, amoxapine, amisulpride, clozapine, aripiprazole, lurasidone, risperidone or perospirone is suitable for treating the subject. In embodiments, the presence of the GG or GT genotype indicates that amitriptyline is suitable for treating the subject. In embodiments, the presence of the GG or GT genotype indicates that amoxapine is suitable for treating the subject. In embodiments, the presence of the GG or GT genotype indicates that amisulpride is suitable for treating the subject. In embodiments, the presence of the GG or GT genotype indicates that clozapine is suitable for treating the subject. In embodiments, the presence of the GG or GT genotype indicates that aripiprazole is suitable for treating the subject. In embodiments, the presence of the GG or GT genotype indicates that lurasidone is suitable for treating the subject. In embodiments, the presence of the GG or GT genotype indicates that risperidone is suitable for treating the subject. In embodiments, the presence of the GG or GT genotype indicates that perospirone is suitable for treating the subject. In embodiments, the presence of the GG or GT genotype indicates that amitriptyline, amoxapine, amisulpride, clozapine, aripiprazole, lurasidone, risperidone or perospirone is suitable for treating the subject.

In an aspect is provided a method of treating a subject for a neuropsychiatric disorder. The method includes: determining a rs7905446 single nucleotide polymorphism (SNP) in the subject; and administering an effective amount of a SSRI or NARI to the subject if a GG or GT genotype is present; or, administering an effective amount of a neuroactive compound other than SSRI or NARI to the subject if a TT genotype is present. Thus, in embodiments the method includes administering an effective amount of a SSRI to the subject if a GG genotype is present. In embodiments, the method includes administering an effective amount of a SSRI to the subject if a GT genotype is present. In embodiments, the method includes administering an effective amount of a NARI to the subject if a GG genotype is present. In embodiments, the method includes administering an effective amount of a NARI to the subject if a GT genotype is present. In embodiments, the method includes administering an effective amount of a SSRI or NARI to the subject if a GG or GT genotype is present. In embodiments, the method includes administering an effective amount of a neuroactive compound other than SSRI to the subject if a TT genotype is present. In embodiments, the method includes administering an effective amount of a neuroactive compound other than NARI to the subject if a TT genotype is present. In embodiments, the method includes administering an effective amount of a neuroactive compound other than SSRI or NARI to the subject if a TT genotype is present.

In an aspect, a method of treating a subject for a neuropsychiatric disorder is provided. The method includes: determining a rs7905446 single nucleotide polymorphism (SNP) in the subject; and administering an effective amount of amitriptyline, amoxapine, amisulpride, clozapine, aripiprazole, lurasidone, risperidone or perospirone to the subject if a GG or GT genotype is present; or, administering an effective amount of a neuroactive compound other than amitriptyline, amoxapine, amisulpride, clozapine, aripiprazole, lurasidone, risperidone or perospirone to the subject if a TT genotype is present. Thus, in embodiments the method includes administering an effective amount of amitriptyline to the subject if a GG or GT genotype is present. In embodiments the method includes administering an effective amount of amoxapine to the subject if a GG or GT genotype is present. In embodiments the method includes administering an effective amount of amisulpride to the subject if a GG or GT genotype is present. In embodiments the method includes administering an effective amount of clozapine to the subject if a GG or GT genotype is present. In embodiments the method includes administering an effective amount of aripiprazole to the subject if a GG or GT genotype is present. In embodiments the method includes administering an effective amount of lurasidone to the subject if a GG or GT genotype is present. In embodiments the method includes administering an effective amount of risperidone to the subject if a GG or GT genotype is present. In embodiments the method includes administering an effective amount of perospirone to the subject if a GG or GT genotype is present. In embodiments the method includes administering an effective amount of amitriptyline, amoxapine, amisulpride, clozapine, aripiprazole, lurasidone, risperidone or perospirone to the subject if a GG or GT genotype is present. In embodiments, the method includes administering an effective amount of a neuroactive compound other than amitriptyline to the subject if a TT genotype is present. In embodiments, the method includes administering an effective amount of a neuroactive compound other than amoxapine to the subject if a TT genotype is present. In embodiments, the method includes administering an effective amount of a neuroactive compound other than amisulpride to the subject if a TT genotype is present. In embodiments, the method includes administering an effective amount of a neuroactive compound other than clozapine to the subject if a TT genotype is present. In embodiments, the method includes administering an effective amount of a neuroactive compound other than aripiprazole to the subject if a TT genotype is present. In embodiments, the method includes administering an effective amount of a neuroactive compound other than lurasidone to the subject if a TT genotype is present. In embodiments, the method includes administering an effective amount of a neuroactive compound other than risperidone to the subject if a TT genotype is present. In embodiments, the method includes administering an effective amount of a neuroactive compound other than perospirone to the subject if a TT genotype is present. In embodiments, the method includes administering an effective amount of a neuroactive compound other than amitriptyline, amoxapine, amisulpride, clozapine, aripiprazole, lurasidone, risperidone or perospirone to the subject if a TT genotype is present.

In another aspect is provided a method of treating a subject for a neuropsychiatric disorder, the subject undergoing treatment with a SSRI or NARI. The method includes: determining a rs7905446 single nucleotide polymorphism (SNP) in the subject; and continuing administration of an effective amount of a SSRI or NARI to the subject if a GG or GT genotype is present; or, discontinuing administration of a SSRI or NARI to the subject if a TT genotype is present and administering an effective amount of a neuroactive compound other than a SSRI or NARI. In embodiments, the subject undergoes treatment with a SSRI. In embodiments, the subject undergoes treatment with a NARI. In embodiments, the subject undergoes treatment with a SSRI or a NARI. In embodiments, the method includes continuing administration of an effective amount of a SSRI to the subject if a GG genotype is present. In embodiments, the method includes continuing administration of an effective amount of a SSRI to the subject if a GT genotype is present. In embodiments, the method includes continuing administration of an effective amount of a SSRI to the subject if a GG or GT genotype is present. In embodiments, the method includes continuing administration of an effective amount of a NARI to the subject if a GG genotype is present. In embodiments, the method includes continuing administration of an effective amount of a NARI to the subject if a GT genotype is present. In embodiments, the method includes continuing administration of an effective amount of a NARI to the subject if a GG or GT genotype is present. In embodiments, the method includes continuing administration of an effective amount of a SSRI or NARI to the subject if a GG or GT genotype is present. In embodiments, the method includes discontinuing administration of a SSRI to the subject if a TT genotype is present and administering an effective amount of a neuroactive compound other than a SSRI. In embodiments, the method includes discontinuing administration of a NARI to the subject if a TT genotype is present and administering an effective amount of a neuroactive compound other than NARI. In embodiments, the method includes discontinuing administration of a SSRI to the subject if a TT genotype is present and administering an effective amount of a neuroactive compound other than a SSRI or NARI. In embodiments, the method includes discontinuing administration of a NARI to the subject if a TT genotype is present and administering an effective amount of a neuroactive compound other than a SSRI or NARI. In embodiments, the method includes discontinuing administration of a SSRI or NARI to the subject if a TT genotype is present and administering an effective amount of a neuroactive compound other than a SSRI or NARI.

In another aspect a method of treating a subject for a neuropsychiatric disorder is provided. The method includes: determining the rs7905446 single nucleotide polymorphism (SNP) in the subject; and continuing administration of amitriptyline, amoxapine, amisulpride, clozapine, aripiprazole, lurasidone, risperidone or perospirone to the subject if a GG or GT genotype is present; or, discontinuing administration of amitriptyline, amoxapine, amisulpride, clozapine, aripiprazole, lurasidone, risperidone or perospirone to the subject if a TT genotype is present and administering an effective amount of a neuroactive compound other than amitriptyline, amoxapine, amisulpride, clozapine, aripiprazole, lurasidone, risperidone or perospirone. In embodiments, the method includes continuing administration of amitriptyline to the subject if a GG genotype is present. In embodiments, the method includes continuing administration of amoxapine GG genotype is present. In embodiments, the method includes continuing administration of amisulpride to the subject if a GG genotype is present. In embodiments, the method includes continuing administration of clozapine to the subject if a GG genotype is present. In embodiments, the method includes continuing administration of aripiprazole to the subject if a GG or is present. In embodiments, the method includes continuing administration of lurasidone to the subject if a GG genotype is present. In embodiments, the method includes continuing administration of risperidone to the subject if a GG genotype is present. In embodiments, the method includes continuing administration of perospirone to the subject if a GG genotype is present. In embodiments, the method includes continuing administration of amitriptyline, amoxapine, amisulpride, clozapine, aripiprazole, lurasidone, risperidone or perospirone to the subject if a GG genotype is present. In embodiments, the method includes continuing administration of amitriptyline to the subject if a GT genotype is present. In embodiments, the method includes continuing administration of amoxapine GT genotype is present. In embodiments, the method includes continuing administration of amisulpride to the subject if a GT genotype is present. In embodiments, the method includes continuing administration of clozapine to the subject if a GT genotype is present. In embodiments, the method includes continuing administration of aripiprazole to the subject if a GT or is present. In embodiments, the method includes continuing administration of lurasidone to the subject if a GT genotype is present. In embodiments, the method includes continuing administration of risperidone to the subject if a GT genotype is present. In embodiments, the method includes continuing administration of perospirone to the subject if a GT genotype is present. In embodiments, the method includes continuing administration of amitriptyline, amoxapine, amisulpride, clozapine, aripiprazole, lurasidone, risperidone or perospirone to the subject if a GT genotype is present. In embodiments, the method includes continuing administration of amitriptyline to the subject if a GG or GT genotype is present. In embodiments, the method includes continuing administration of amoxapine GG or GT genotype is present. In embodiments, the method includes continuing administration of amisulpride to the subject if a GG or GT genotype is present. In embodiments, the method includes continuing administration of clozapine to the subject if a GG or GT genotype is present. In embodiments, the method includes continuing administration of aripiprazole to the subject if a GG or GT genotype is present. In embodiments, the method includes continuing administration of lurasidone to the subject if a GG or GT genotype is present. In embodiments, the method includes continuing administration of risperidone to the subject if a GG or GT genotype is present. In embodiments, the method includes continuing administration of perospirone to the subject if a GG or GT genotype is present. In embodiments, the method includes continuing administration of amitriptyline, amoxapine, amisulpride, clozapine, aripiprazole, lurasidone, risperidone or perospirone to the subject if a GG or GT genotype is present. In embodiments, the method includes discontinuing administration of amitriptyline to the subject if a TT genotype is present and administering an effective amount of a neuroactive compound other than amitriptyline. In embodiments, the method includes discontinuing administration of amoxapine to the subject if a TT genotype is present and administering an effective amount of a neuroactive compound other than amoxapine. In embodiments, the method includes discontinuing administration of amisulpride to the subject if a TT genotype is present and administering an effective amount of a neuroactive compound other than amisulpride. In embodiments, the method includes discontinuing administration of clozapine to the subject if a TT genotype is present and administering an effective amount of a neuroactive compound other than clozapine. In embodiments, the method includes discontinuing administration of aripiprazole to the subject if a TT genotype is present and administering an effective amount of a neuroactive compound other than aripiprazole. In embodiments, the method includes discontinuing administration of lurasidone to the subject if a TT genotype is present and administering an effective amount of a neuroactive compound other than lurasidone. In embodiments, the method includes discontinuing administration of risperidone to the subject if a TT genotype is present and administering an effective amount of a neuroactive compound other than risperidone. In embodiments, the method includes discontinuing administration of perospirone to the subject if a TT genotype is present and administering an effective amount of a neuroactive compound other than perospirone. In embodiments, the method includes discontinuing administration of amitriptyline to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of amoxapine to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of amisulpride to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of clozapine to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of aripiprazole to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of lurasidone to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of risperidone to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of perospirone to the subject if a TT genotype is present and administering an effective amount of a neuroactive compound other than amitriptyline, amoxapine, amisulpride, clozapine, aripiprazole, lurasidone, risperidone or perospirone. In embodiments, the method includes discontinuing administration of amitriptyline, amoxapine, amisulpride, clozapine, aripiprazole, lurasidone, risperidone or perospirone to the subject if a TT genotype is present and administering an effective amount of a neuroactive compound other than amitriptyline, amoxapine, amisulpride, clozapine, aripiprazole, lurasidone, risperidone or perospirone.

In another aspect a method of detecting a single nucleotide polymorphism (SNP) in a subject is provided. The method includes detecting in a biological sample from said subject the presence of a rs7905446 single nucleotide polymorphism (SNP). In embodiments, the subject has a neuropsychiatric disorder. In embodiments, the subject is at risk of having a neuropsychiatric disorder. In embodiments, the subject has or is at risk of having a neuropsychiatric disorder.

For the methods provided herein the treatment may include a SSRI. In embodiments the SSRI is paroxetine. In embodiments the SSRI is fluoxetine. In embodiments the SSRI is citalopram. In embodiments the SSRI is escitalopram. In embodiments the SSRI is paroxetine, fluoxetine, citalopram or escitalopram.

For the methods provided herein the treatment may include a NARI. In embodiments, the NARI is desipramine. In embodiments, the NARI is nortyptiline. In embodiments, the NARI is bupropion. In embodiments, the NARI is mirtazapine. In embodiments, the NARI is maprotiline. In embodiments, the NARI is atomoxetine. In embodiments, the NARI is desipramine, nortyptiline, bupropion, mirtazapine, maprotiline or atomoxetine.

For the methods provided herein, the method may include detecting the rs7905446 single nucleotide polymorphism (SNP). In embodiments, the method includes detecting the rs7905446 SNP by 5' exonuclease polymerase chain reaction. In embodiments, the method includes detecting the rs7905446 SNP by DNA sequencing. In embodiments, the method includes detecting the rs7905446 SNP by restriction fragment length polymorphism. In embodiments, the method includes detecting the rs7905446 SNP by chip hybridization. In embodiments, the method includes detecting the rs7905446 SNP by single base extension assay. In embodiments, the method includes detecting the rs7905446 SNP by 5' exonuclease polymerase chain reaction, DNA sequencing, restriction fragment length polymorphism, chip hybridization or single base extension assay.

For the methods provided herein, the method may include obtaining a biological sample from the subject. In embodiments, the biological sample includes blood. In embodiments, the biological sample includes cheek swab. In embodiments, the biological sample includes orally obtained cells. In embodiments, the biological sample includes skin biopsy. In embodiments, the biological sample includes blood, cheek swab or orally obtained cells, or skin biopsy.

For the methods provided herein, the method may include obtaining a biological sample from the subject for determining the rs7905446 single nucleotide polymorphism (SNP) in the subject. In embodiments, the biological sample includes blood. In embodiments, the biological sample includes cheek swab. In embodiments, the biological sample includes orally obtained cells. In embodiments, the biological sample includes skin biopsy. In embodiments, the biological sample includes blood, cheek swab or orally obtained cells, or skin biopsy.

For the methods provided herein, the method may further include detecting a rs6583737, rs12254390, or rs111631884 SNP. In embodiments, the method further includes detecting a rs6583737, SNP. In embodiments, method further includes detecting a rs12254390 SNP. In embodiments, method further includes detecting a rs111631884 SNP.

As described above, the methods provided herein may determine whether a neuroactive drug is suitable for treating a subject undergoing treatment for a neuropsychiatric disorder. Thus, for the methods provided herein, the neuropsychiatric disorder includes bipolar disorder. In embodiments, the neuropsychiatric disorder includes unipolar depression. In embodiments, the neuropsychiatric disorder includes obsessive-compulsive disorder. In embodiments, the neuropsychiatric disorder includes eating disorder. In embodiments, the neuropsychiatric disorder includes migraine. In embodiments, the neuropsychiatric disorder includes bipolar disorder, unipolar depression, obsessive-compulsive disorder, eating disorder, or migraine.

The methods provided herein may include treating a subject for a neuropsychiatric disorder. In embodiments, the neuropsychiatric disorder includes bipolar disorder. In embodiments, the neuropsychiatric disorder includes unipolar depression. In embodiments, the neuropsychiatric disorder includes obsessive-compulsive disorder. In embodiments, the neuropsychiatric disorder includes eating disorder. In embodiments, the neuropsychiatric disorder includes migraine. In embodiments, the neuropsychiatric disorder includes bipolar disorder, unipolar depression, obsessive-compulsive disorder, eating disorder, or migraine.

In an aspect is provided a kit for predicting the suitability of a neuroactive compound in a subject with a neuropsychiatric disorder. The kit includes at least one nucleic acid probe or primer for detecting a rs7905446 single nucleotide polymorphism (SNP). In embodiments, the kit further includes at least one nucleic acid probe or primer for detecting a rs6583737 single nucleotide polymorphism (SNP). In embodiments, the kit further includes at least one nucleic acid probe or primer for detecting a rs12254390 single nucleotide polymorphism (SNP). In embodiments, the kit further includes at least one nucleic acid probe or primer for detecting a rs111631884 single nucleotide polymorphism (SNP). In embodiments, the kit further includes at least one nucleic acid probe or primer for detecting a rs6583737, rs12254390, or rs111631884 single nucleotide polymorphism (SNP).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Materials and Methods

Pooled DNA sequencing. DNA was quantified with PicoGreen and equal quantities from each subject were combined into 48 pools (ranging from 11 to 24 subjects per pool) grouped by medication (citalopram, paroxetine, fluoxetine, sertraline and lithium) and type of response (good, moderate and poor). The entire HTR7 gene, promoter and 5' and 3' UTR regions were covered and amplified by 13 long range PCR, generating DNA fragments from 10 to 13 kb covering the region of Chr10: 92499978-92623668. We performed 2×150 bp paired-end, multiplexed sequencing on an Illumina MiSeq sequencer (Illumina, San Diego, Calif.). The quality of raw-reads were examined using FastQC [34] and were aligned to human reference genome (GRCh37/hg19) using BWA [35]. We used CRISP (v0.7) [36] with the default setting as the variant caller and filtered the variants in the VCF files that showed EMpass, quality value >100 and minor allele frequency >0.05. The variants were annotated by ANNOVAR [37].

SNP genotyping. Genotyping of rs7905446 (T/G) was performed using TaqMan SNP genotyping assay on 7900HT Fast Real-Time PCR System (Thermo Fisher Scientific, Waltham, Mass., USA) as previously described [45]. The assay included negative controls and was run with the following condition: 95° C. for 10 min followed by 40 cycles of 92° C. for 15 s and 60° C. for 1 min. The genotyping success rate was >95%. Twenty percent of the samples were genotyped in duplicate, with 100% reproducibility.

Transfection and luciferase reporter assay. HTR7 promoter containing rs7905447(T/G) SNP was amplified from subjects harboring either homozygous rs7905446-T allele or rs7905446-G allele by primers flanking NheI/HindIII restriction sites (5'-TAAGCAAAGCTTAAT-TCCCCTTGGTATCCAAACCC-3' (SEQ ID NO:1) and 5'-TAAGCAGCTAGCATATTGCTTTGTGGCCTAGGT-ATT-3' (SEQ ID NO:2)). After double digestion, HTR7 promoter fragments were ligated into digested pGL4.26 [luc2/minP/Hygro] luciferase reporter vector (Promega, Madison, Wis., USA). Several clones of rs79054446-T and rs7905446-G vectors were verified by sequencing analysis. HT-22 and SK-N-MC cell lines were cultured in RPMI-1640 medium supplemented with 10% fetal bovine serum, 2 mM L-glutamine and antibiotics. Cells (20,000 cells/well of a 96-well plate) were transfected with 90 ng of rs79054446-T or rs7905446-G vectors together with 10 ng of pGL4.74 [hRluc/TK] Renilla Luciferase control vector (Promega) using Lipofectamine 3000 reagent (Thermo Fisher Scientific). 17β-estradiol was dissolved in 100% ethanol and cells were treated with different concentrations for 24 h. Cells were assayed for luciferase and renilla luciferase activity using Dual-Glo Luciferase Assay System (Promega) on GloMAX luminometer plate reader (Promega). Firefly luciferase activity in each sample was normalized for renilla luciferase activity according to the manufacturer's instruction.

Electrophoretic mobility shift assay (EMSA). EMSA was performed using the LightShift Chemiluminescent EMSA kit (Thermo Fisher Scientific) according to the manufacturer's protocol. In brief, nuclear extracts of Hela cells were prepared using NE-PER™ nuclear and cytoplasmic extraction kit (Thermo Fisher Scientific). The binding reaction was performed using 5 µg of nuclear protein and biotin-labeled probes spanning rs7905446 (T/G) region and were incubated at room temperature for 40 min (5'-GAGTCAGAG-GAAGAGTT/GGAATATAATACCTAGGC-3'(SEQ ID NO:3 and SEQ ID NO:4)). The competition reaction was performed using 200-fold molar excess of unlabeled probe. For supershift analysis, 1 µg anti-CEBPB antibody (Santa Cruz Biotechnology, Inc., Dallas, Tex., USA) was added to the nuclear extract prior to the binding reaction and incubated on ice for 40 min. The DNA-protein complexes were separated via electrophoresis followed by transferring to Biodyne™ nylon membrane (Thermo Fisher Scientific) and detected using chemiluminescence.

Statistical analysis. The association between drug response and allelic SNPs identified from pooled-sequencing were performed using logistic regression (PLINK version 1.9). [46]. The association between drug response and rs7905446 genotype was performed using logistic regression within Caucasian population. $\chi^2$ tests were used to compare the sex distribution between responder and nonresponder. Group differences were analyzed using Student's T-test. P value<0.05 were considered statistically significant.

Example 2

Pool-Sequencing of HTR7 Gene Identifies Common Variants Influencing Response to Antidepressants We used a cost-effective pool-sequencing strategy to sequence the whole HTR7 gene and its regulator regions to investigate the association of common variations in HTR7 and response to four selective serotonin reuptake inhibitors (SSRIs, including citalopram, paroxetine, fluoxetine and sertraline) and lithium in a retrospective cohort mainly consisting of BD. We found 80 SNPs with FDR<0.05 associated with response to paroxetine. Among the significant SNPs, rs7905446 (T/G) which is located at the promoter region also showed nominal significance (p<0.05) in fluoxetine group. Taqman assay validated the sequencing result of rs7905446. Logistic regression demonstrated rs7905446 GG/TG genotypes and female gender were associated with better response to two SSRIs (paroxetine and fluoxetine). In the second stage, we investigated if rs7905446 could predict antidepressant response in two prospective cohorts consisting of unipolar depression (MARS and GENDEP cohorts). We replicated the results observed in the BD cohort and found GG/TG genotypes could predict treatment remission, especially in SSRI. Functional study of rs7905446 showed that G allele displayed higher luciferase activity compared to T allele in two neuronal related cell lines and estrogen treatment decreased the activity of only G allele. Electrophoretic mobility shift assay suggested G allele interacted with CEBPB transcription factor (TF) while T allele did not show any interaction potential with TF. Our results provided novel pharmacogenomic evidence to support a role of HTR7 in predicting antidepressant response, particularly in genetic marker rs7905446.

In this report, in a first stage, we utilized a cost-effective pool-sequencing strategy to sequence the entire HTR7 gene and its regulatory regions in a retrospective cohort mainly consisting of BD, aimed to investigate the genetic association of HTR7 and antidepressants/lithium response. In the second stage, in two different prospective cohorts consisting of unipolar depression, we replicated the findings from bipolar depression and showed that common variations in HTR7 were associated with response to antidepressants.

Pooled-Sequencing of HTR7 Gene in a Retrospective Cohort

Subjects. All subjects (n=497) were ascertained as part of several cohorts collected for genetic studies of BD. Subjects were identified through VA and UCSD clinics, as well as, advertisement and patient support groups. All subjects provided written informed consent according to UCSD IRB approved procedures and consent form.

Assessment of SSRI response. All subjects were directly interviewed using the Diagnostic Interview for Genetic Studies (DIGS) [33] which had been modified to collect information regarding past drug trials. Interviewers underwent a training course, reliability was tested regularly and was consistently high. Information from the modified DIGS was reviewed by a panel of experienced clinicians along with medical records and information from family informants. Subjects with a BD, major depressive disorder (MDD) or schizoaffective disorder bipolar type (SABP) diagnosis were included in the study. Patients were queried regarding all their past medication trials including a past history of SSRI treatment. Subject's response to SSRI's over their lifetime was assessed based on self-reporting. Blind raters considered all information about all SSRI trials over the patient's life in order to assess response. Good responders were those who were estimated to have 50% reduction in symptoms or episodes. Subject demographic information classified by treatment groups is shown in Table 2.

TABLE 2

Clinical characteristics of the study groups underwent pooled-DNA sequencing.

| Treatment | N | Males (%) | Age (years)[1] | Ethnicity (% Caucasian) | BP vs MDD vs SABP (%) |
|---|---|---|---|---|---|
| Citalopram | | | | | |
| Good responder | 16 | 50.0 | 44 (35, 53) 22-58 | 100.0 | 100 vs 0 vs 0 |
| Moderate/poor responder | 51 | 58.8 | 46 (36, 51) 24-67 | 86.3 | 96.1 vs 2 vs 2 |
| Paroxetine | | | | | |
| Good responder | 26 | 50.0 | 49 (41, 55) 22-70 | 92.3 | 80.7 vs 15.4 vs 3.8 |
| Moderate/poor responder | 109 | 69.7 | 47 (38, 53) 20-72 | 93.6 | 97.2 vs 2.8 vs 0 |
| Fluoxetine | | | | | |
| Good responder | 80 | 47.5** | 45 (36, 53) 20-84 | 96.3 | 80.1 vs 16.3 vs 3.8 |
| Moderate/poor responder | 143 | 65.7 | 47 (37, 53) 21-76 | 89.5 | 95.1 vs 4.2 vs 0.7 |
| Sertraline | | | | | |
| Good responder | 58 | 48.3 | 44 (37, 54) 18-72 | 89.7 | 86.2 vs 10.3 vs 3.4 |
| Moderate/poor responder | 111 | 59.5 | 47 (37, 54) 21-68 | 88.3 | 93.7 vs 6.3 vs 0 |
| Lithium | | | | | |
| Good responder | 144 | 44.4* | 47 (38, 54) 20-80 | 97.9 | 95.8 vs 0 vs 4.2 |
| Moderate/poor responder | 157 | 56.7 | 45 (37, 53) 15-72 | 98.1 | 94.9 vs 0 vs 5.1 |

SSRI: Selective serotonin reuptake inhibitors; BP: Bipolar disorder; MDD: Major depressive disorder; SABP: Schizoaffective disorder, bipolar type.
[1]Median (25th, 75th percentile) range
*$P < 0.05$,
**$P < 0.01$ Replication study I in the Munich Antidepressant Response Signature (MARS) project. The MARS project is a prospective naturalistic study of adult inpatients of depression in Germany [31,38]. Subjects were aged 18 to 75 years and Caucasian ancestry. Diagnoses were obtained by trained psychiatrists based on diagnostic and statistical manual of mental diseases (DSM-IV) criteria of a major depressive episode, including first-episode MDD, recurrent MDD and BD. Treatment was selected naturalistically by clinicians and included flexible dosage of antidepressants and augmenting agents. The severity of the psychopathologic abnormality was assessed based on the 21-item Hamilton Depression Rating Scale (HDRS) [39], administered weekly by trained psychiatrists and psychologists. MARS was approved by the ethics committee of Ludwig Maximilians University, and all participants provided written consent after the study protocol and potential risks were explained. In this study, we evaluated the treatment response at week 6 and defined remission as HDRS<10, response as HDRS decrease≥50% and non-response as HDRS decrease<50%.

Replication study II in the Genome-based Therapeutic Drugs for Depression (GENDEP) study. GENDEP is a multicenter part-randomized open-label pharmacogenetic study of 811 outpatients with moderate to severe unipolar depression diagnosed according to DSM-IV and established in the semi-structured SCAN interview [40]. Patients were aged 19 to 72 years with European ancestry for at least two generations. Patients with personal and family history of schizophrenia or bipolar affective disorder and current dependence on alcohol or drugs were excluded from the study. Two antidepressants, escitalopram and nortriptyline were randomly allocated to patients for 12 weeks. Patients with contraindications for one of the drugs were allocated nonrandomly to the other antidepressant. Response was assessed weekly from week 0 to week 12 by three established measures of depression severity: the clinician-rated 10-item Montgomery-Åsberg Depression Rating Scale (MADRS) [41], the HDRS-17 [42] and self-reported 21-item Beck Depression Inventory [43], among which the MADRS proved to be the most internally consistent and informative of the three scales [44]. The study was approved by ethics boards of all the participating centers. All participants provided written informed consent. In this study, we evaluated the treatment response at week 12 and defined remission as MADRS≤10, response as MADRS decrease≥50% and non-response as MADRS decrease≤50%.

Figure 2:
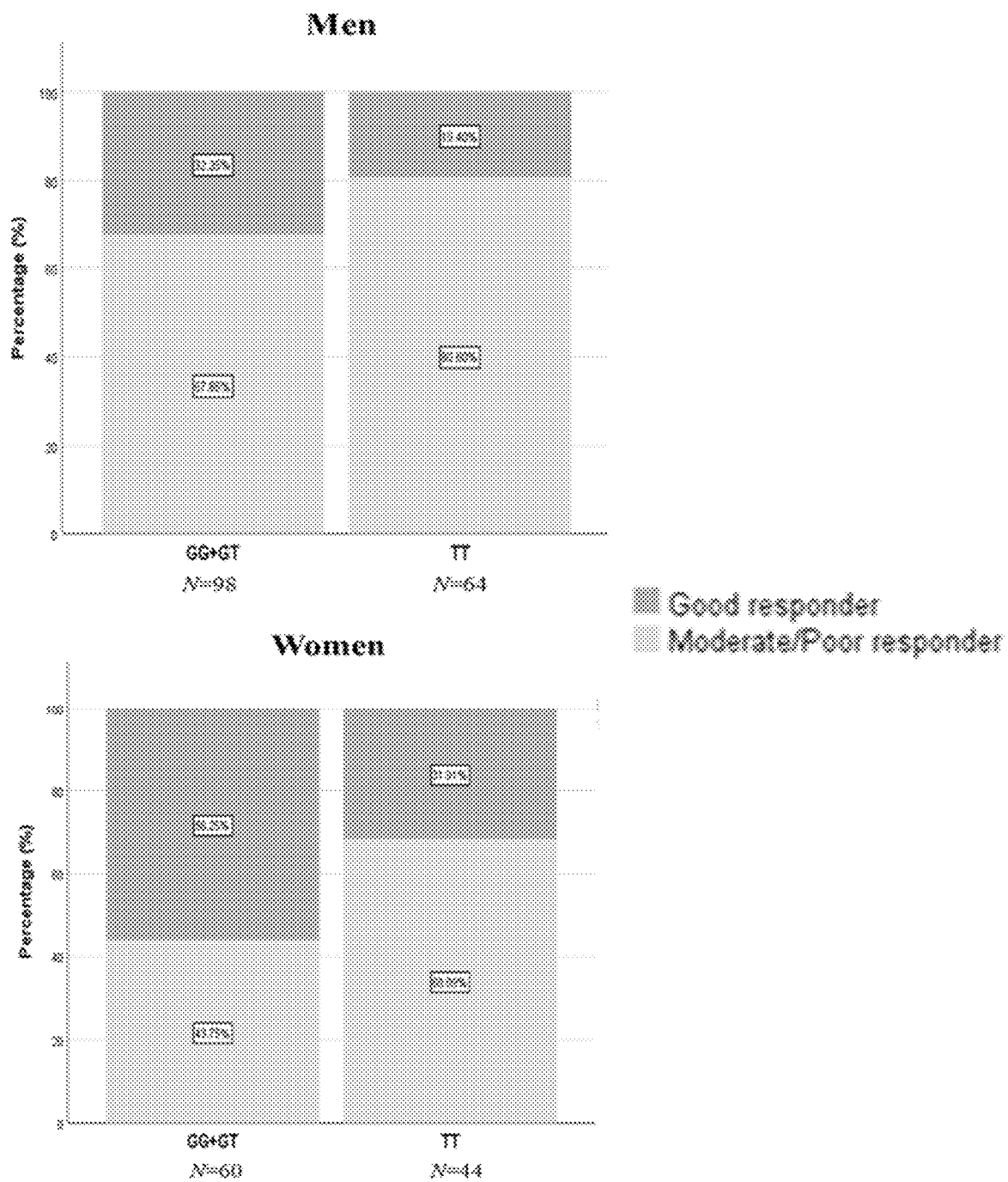
FIG. 2. Women gender and individual with rs7905446 GG/GT genotypes showed better response to SSRIs (paroxetine+fluoxetine).

Common SNPs in HTR7 are associated with SSRI response in BD. In the retrospective cohort, the majority of the patients were Caucasian ethnicity and with BD diagnosis (Table 2). We performed pooled-sequencing of HTR7 gene in total of 497 subjects and examined the association between treatment response and common SNP variations based on an allelic model. We found that 80 SNPs survived FDR<0.05 in the paroxetine group and 95% (n=76) of those SNPs were located at intron regions. One of the top SNPs rs7905446, located at the promoter region, is significantly associated with paroxetine response (FDR=0.0387, Table 3). Interestingly, rs7905446 also showed nominal significance (P=0.047) in the fluoxetine group. Rs7905446 is in high linkage disequilibrium with several other top SNPs in the 5' upstream (rs6583737 and rs12254390) and intron (rs111631884) regions (FIG. 1). We validated rs7905446 in Caucasian subjects using TaqMan SNP genotyping assay in both paroxetine and fluoxetine groups (n=266). The genotype distribution was significantly different between responders and non-responders of these two SSRIs (Responders: TT vs GT vs GG=29.7% vs 54.9% vs 15.4%; Non-responders: TT vs GT vs GG=46.0% vs 41.5% vs 12.5%; Pearson $\chi^2$=6.697, P=0.035). Next, using logistic regression we found that TT genotype was significantly associated with poor paroxetine response compared with TG/GG genotypes, when controlled for sex and age (P=0.005, OR=5.250; Table 4). When combining both paroxetine and fluoxetine groups, TT genotype was again shown to be associated with poor response in two SSRIs (TT vs TG/GG: P=0.008, OR=2.135; Table 4 and FIG. 2). Gender seemed to influence SSRI response in our BD samples, specifically, men were more likely to become poor responders (P<0.001, OR=2.623; Table 4 and FIG. 2). No sex×rs7905446 interaction was found in either the paroxetine group or paroxetine+fluoxetine groups. Four SNPs in the fluoxetine group and three SNPs in the lithium group were with nominal P<0.05. No SNPs with nominal P<0.05 were detected in citalopram and sertraline groups.

TABLE 3

Top SNPs in HTR7 gene in response to paroxetine.

|  | SNP | Ref | Alt | P-value | FDR |
|---|---|---|---|---|---|
| 5' upstream | rs6583737* | A | G | 0.001346 | 0.0134 |
|  | rs12254390* | G | C | 0.008268 | 0.0241 |
|  | rs1935346 | T | C | 0.008589 | 0.0244 |
| Promoter | rs7905446* | T | G | 0.01695 | 0.0387 |
| Intron | rs4262637 | T | C | 9.31e-05 | 0.007868 |
|  | rs7912164 | T | C | 5.14e-05 | 0.007868 |
|  | rs111631884* | T | G | 0.00015 | 0.008709 |

*In high linkage with each other.

TABLE 4

Association between HTR7 promoter rs7905446 and antidepressants response in Caucasian subjects of three cohorts

|  | β | OR | P-value |
|---|---|---|---|
| Retrospective cohort (responder vs. non-responder) Paroxetine (n = 124) | | | |
| Rs7905446 | 1.658 | 5.250 | 0.005[a] |
| Sex | 1.059 | 2.883 | 0.033[b] |
| Age | -0.02 | 0.973 | 0.191 |
| Paroxetine + fluoxetine (n = 266) | | | |
| Rs7905446 | 0.758 | 2.135 | 0.008[a] |
| Sex | 0.964 | 2.623 | <0.001[b] |
| Age | -0.005 | 0.995 | 0.649 |
| Prospective MARS cohort (remitter vs. non-remitter) SSRI (n = 253) | | | |
| Rs7905446 | 0.681 | 1.976 | 0.0169[a] |
| Sex | -0.310 | 0.733 | 0.272 |
| Age | -0.013 | 0.987 | 0.190 |
| SSRI + SNRI (n = 542) | | | |
| Rs7905446 | 0.378 | 1.460 | 0.044[a] |
| Sex | -0.319 | 0.727 | 0.086 |
| Age | 0.0009 | 1.001 | 0.897 |

TABLE 4-continued

Association between HTR7 promoter rs7905446 and antidepressants response in Caucasian subjects of three cohorts

|  | β | OR | P-value |
|---|---|---|---|
| All antidepressants (n = 837) | | | |
| Rs7905446 | 0.326 | 1.385 | 0.032[a] |
| Sex | -0.156 | 0.856 | 0.299 |
| Age | 0.0003 | 1.000 | 0.958 |
| Prospective GENDEP cohort (remitter vs. non-remitter) Escitalopram (n = 432) | | | |
| Rs7905446 | 0.512 | 1.669 | 0.008[c] |
| Sex | -0.297 | 0.743 | 0.178 |
| Age | -0.036 | 0.970 | 0.001 |
| Center ID | 0.010 | 1.01 | 0.681 |
| Nortriptyline (n = 328) | | | |
| Rs7905446 | -0.366 | 0.694 | 0.154 |
| Sex | -0.280 | 0.889 | 0.302 |
| Age | -0.004 | 0.996 | 0.713 |
| Center ID | -0.035 | 0.966 | 0.219 |
| Escitalopram + nortriptyline (n = 730) | | | |
| Rs7905446 | 0.132 | 1.141 | 0.390 |
| Sex | -0.112 | 0.894 | 0.476 |
| Age | -0.024 | 0.976 | <0.001 |
| Center ID | -0.007 | 0.993 | 0.720 |

SSRI: Selective serotonin reuptake inhibitors: SNRI: Serotonin and norepinephrine reuptake inhibitors.
[a]TT vs TG/GG using logistic regression adjusted for sex and age.
[b]Men vs women using logistic regression adjusted for rs7905446 and age.
[c]TT vs TG/GG using logistic regression adjusted for sex, age and center ID.

rs7905446 is associated with antidepressant response in unipolar depression in MARS and GENDEP cohorts. We next investigated if rs7905446 was associated with antidepressant response in unipolar depression within two large-scale prospective cohorts. The treatment in MARS cohort is naturalistic selected by clinician which contains a variety of antidepressants including SSRIs, SNRIs and tricyclics etc. We first examined if rs7905446 can predict antidepressant response in general, i.e. including all antidepressant drugs. We found TT genotypes significantly associated with non-remitters while TG/GG genotypes predicted treatment remission at week 6, when controlled for sex and age (TT vs TG/GG: P=0.032, OR=1.385; Table 4). Next, we found similar results in patients underwent SSRI or SNRI treatments (P=0.044, Table 4) or only treated by SSRI (P=0.017, Table 4). Other top SNPs (rs6583737, rs12254390 and rs111631884) that are in high linkage with rs7905446 showed similar predictive effects. In GENDEP cohort, two antidepressants (escitalopram and nortriptyline) that represent the two most common mechanisms of action of antidepressants were part-randomized given to the patients. Interestingly, we found TG/GG genotypes predict remission in escitalopram (an SSRI) but not nortriptyline. No significant gender effect was found to predict the response to antidepressants in the MARS and GENDEP cohorts.

Figure 3:
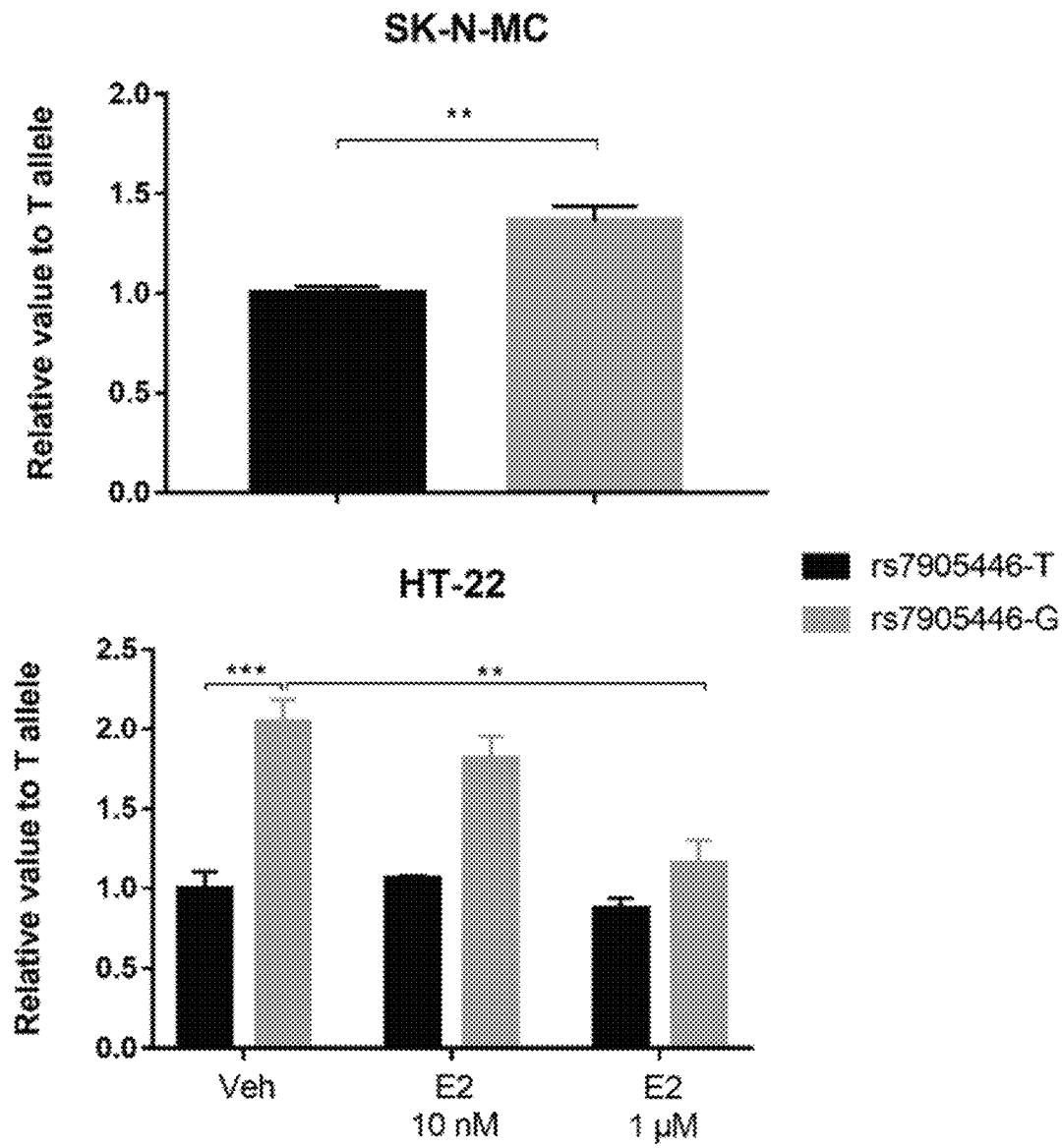
FIG. 3. Rs7905446-G allele displayed higher luciferase activity compared with rs7905446-T tested in two cell lines. High concentration of β-estradiol (E2) treatment significantly reduced the activity only in G allele. $P<0.01$; *$P<0.001$.
Figure 4:
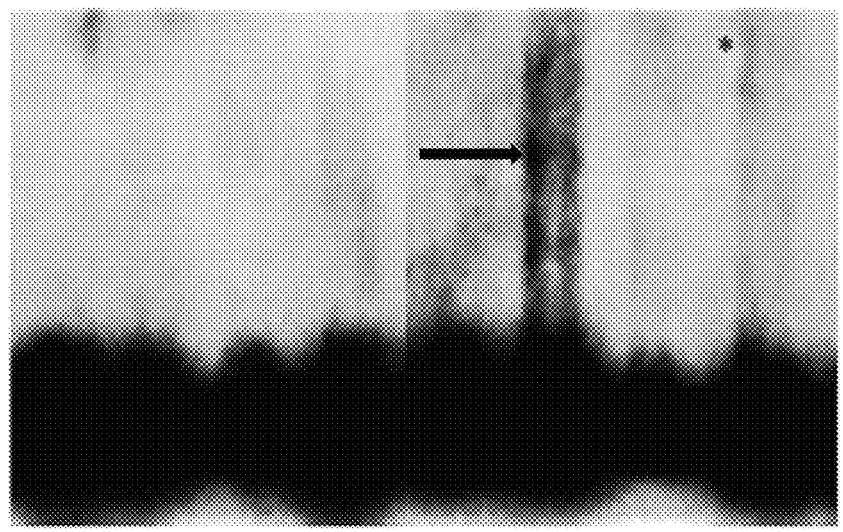
FIG. 4. Electrophoretic mobility shift assay showed biotin-labeled probe containing rs7905446-G can produce a shift (arrow) when incubated with HeLa cell nuclear extract, suggesting an interaction with transcription factors. An anti-CEBPB antibody generated a supershift (asterisk) suggesting an interaction with CEBPB transcription factor.

Functional validation of rs7905446. We used luciferase reporter assay to test if rs7905446 was a functional SNP in two neuronal related cell lines, SK-N-MC (neuroblastoma cell line) and HT-22 (mice hippocampal cell line). In both cell lines we observed rs7905446-G allele that linked with better antidepressant response exhibited stronger luciferase signals compared with T allele, suggesting a higher promoter activity (SK-N-MC: P<0.01; HT22: P<0.001; FIG. 3). Sex seemed to play a role in modulating antidepressant response and we found men were more than two folds chance to become non-responders in the BP retrospective samples (Table 4), suggesting estrogen may enhance the effect of antidepressant treatment. We treated HT-22 cell line with different concentrations of estrogen and found the high activity of rs7905446-G allele was decreased after estrogen treatment at a concentration of 1 μM while the activity of T allele was not influenced at any concentration tested (FIG. 3). The ENCODE database suggests rs7905446 position overlaps with the binding sites of several potential transcription factors (TFs), including CEBPB, which can recruit both activators like EP300 and repressors like estrogen receptor 1 (ESR1) [47,48]. Electrophoretic mobility shift assay showed rs7905446-G allele was able to generate a shift and when adding an anti-CEBPB antibody a supershift was observed. In contrast, biotin-probe spanning T allele did not show binding potentials of any TFs in the nuclear extract (FIG. 4).

Discussion. Changes in 5-HT levels have been associated with several neuropsychiatric disorders including obsessive-compulsive disorder, eating disorder, migraine, depression and BD. The effects of 5-HT were transduced through 5-HT receptors, among which HTR7 displays the highest affinity for 5-HT [4]. HTR7 is involved in a variety of behavioral and physiological functions, e.g. sleep, circadian rhythm, thermoregulation, learning, memory, cognition, mood and emotional process [17, 49-51]. Taking the advantage of second-generation technology, we used a cost-effective strategy to pool-seq the whole HTR7 gene in a large sample set, enabling us to comprehensively investigate the genetic variations contained in a window of ~13 kb in the HTR7 gene. We first found the association of HTR7 variation and antidepressant response in a retrospective cohort mainly consist of BD. Since HTR7 has large intron regions, we found 76 of the 80 SNPs that survived FDR<0.05 in paroxetine group were located at introns and no exonic SNPs were significant. Of particular interest is SNP rs7905446 (T/G) located at the promoter region because a number of cancer cell lines validated TFs show binding potential around this region, which implicated this maybe a functional SNP. By using Taqman assay we validated the sequencing results and showed TT genotype was significantly associated with poor response in two SSRIs, paroxetine and fluoxetine.

In the second stage, we replicated the association of rs7905446 and antidepressant response in two prospective cohorts with unipolar diagnosis (MARS and GENDEP cohorts). We found rs7905446 could predict remission of SSRI in both cohorts. In GENDEP cohort, we noticed that rs7905446 can predict remission in escitalopram but not nortriptyline. These two drugs represent two most common mechanisms of action among commonly used antidepressants. Escitalopram is a highly selective inhibitor of the serotonin transporter with no direct effect on norepinephrine transporter. In contrast, nortriptyline is a tricyclic antidepressant with a hundred times higher affinity to norepinephrine transporter than for the serotonin transporter [40]. Our result suggested HTR7 polymorphisms are more strongly associated with response to SSRI than NARI. Similar in the MARS cohort, rs7905446 in predicting remission to SSRI exhibited a much lower p-value than that in predicting SSRI+SNRI together. We also found that gender seemed to affect antidepressant response in BD cohort but not in the two depression cohorts, implying men and women may respond differentially to antidepressants and gender may play different roles in BD and unipolar depression. Indeed, in accordance with our findings in the BD cohort, there are reports suggesting SSRI are more effective in women than in men [53,54]. While most studies showed an almost equal gender ratio in lifetime prevalence in BD, women were twice as likely than men to suffer unipolar depression [54, 55].

In the functional study of rs7905446 we found G allele that associated with better antidepressants response displayed higher promoter activity than T allele, while estrogen treatment only decreased the promoter activity containing G allele. A number of studies have suggested estrogen as antidepressants or as coadjuvants to facilitate the effect of antidepressants like fluoxetine [56]. Our results suggested estrogen may underly why women showed superior response to SSRI than men. In addition, we revealed a novel mechanism how estrogen exerted antidepressant effect which is through decreasing HTR7 expression. EMSA experiment showed only G allele interacted with TF binding. An anti-CEBPB antibody generated a supershift band suggesting CEBPB may serve as a TF modulating HTR7 expression. CEBPB can recruit both activators like EP300 and repressors like ESR1 [47, 48].

In conclusion, our study showed a functional SNP rs7905446 can predict response to antidepressants in both BD and unipolar depression, providing a novel pharmacogenetic marker for clinical diagnosis.

```
INFORMAL SEQUENCE LISTING
                                             SEQ ID NO: 1
TAAGCAAAGCTTAATTCCCCTTGGTATCCAAACCC

SEQ ID NO: 2
TAAGCAGCTAGCATATTGCTTTGTGGCCTAGGTATT

SEQ ID NO: 3
GAGTCAGAGGAAGAGTTGAATATAATACCTAGGC

SEQ ID NO: 4
GAGTCAGAGGAAGAGTGGAATATAATACCTAGGC
```

REFERENCES

1. Hannon J, Hoyer D. Molecular biology of 5-HT receptors. Behav Brain Res 2008; 195: 198-213.
2. Nichols D E, Nichols C D. Serotonin receptors. Chem Rev 2008; 108: 1614-1641.
3. Bard J A, Zgombick J, Adham N et al. Cloning of a novel human serotonin receptor (5-HT7) positively linked to adenylate cyclase. J Biol Chem 1993; 268: 23422-23426.
4. Ruat M, Traiffort E, Leurs R et al. Molecular cloning, characterization, and localization of a high-affinity serotonin receptor (5-HT7) activating cAMP formation. Proc Natl Acad Sci USA 1993; 90: 8547-8551.
5. Neumaier J F, Sexton T J, Yracheta J et al. Localization of 5-HT(7) receptors in rat brain by immunocytochemistry, in situ hybridization, and agonist stimulated cFos expression. J Chem Neuroanat 2001; 21: 63-73.
6. Varnas K, Thomas D R, Tupala E et al. Distribution of 5-HT7 receptors in the human brain: a preliminary autoradiographic study using [3H]SB-269970. Neurosci Lett 2004; 367: 313-316.
7. Beattie D T, Smith J A. Serotonin pharmacology in the gastrointestinal tract: a review. Naunyn Schmiedebergs Arch Pharmacol 2008; 377: 181-203.
8. East S Z, Burnet P W, Kerwin R W, Harrison P J. An RT-PCR study of 5-HT(6) and 5-HT(7) receptor mRNAs in the hippocampal formation and prefrontal cortex in schizophrenia. Schizophr Res 2002; 57: 15-26.
9. Mowry B J, Ewen K R, Nancarrow D J et al. Second stage of a genome scan of schizophrenia: study of five positive regions in an expanded sample. Am J Med Genet 2000; 96: 864-869.

10. Ikeda M, Iwata N, Kitajima T et al. Positive association of the serotonin 5-HT7 receptor gene with schizophrenia in a Japanese population. Neuropsychopharmacology 2006; 31: 866-871.
11. Kim J H, Park B L, Cheong H S et al. Association between HTR7 genetic polymorphisms and alcohol dependence, using the alcohol use disorders identification test (AUDIT). Alcohol Clin Exp Res 2014; 38: 2354-2361.
12. Zlojutro M, Manz N, Rangaswamy M et al. Genome-wide association study of theta band event-related oscillations identifies serotonin receptor gene HTR7 influencing risk of alcohol dependence. Am J Med Genet B Neuropsychiatr Genet 2011; 156B: 44-58.
13. Hedlund P B, Sutcliffe J G. The 5-HT7 receptor influences stereotypic behavior in a model of obsessive-compulsive disorder. Neurosci Lett 2007; 414: 247-251.
14. Ballaz S J, Akil H, Watson S J. Analysis of 5-HT6 and 5-HT7 receptor gene expression in rats showing differences in novelty-seeking behavior. Neuroscience 2007; 147: 428-438.
15. Guscott M, Bristow L J, Hadingham K et al. Genetic knockout and pharmacological blockade studies of the 5-HT7 receptor suggest therapeutic potential in depression. Neuropharmacology 2005; 48: 492-502.
16. Sarkisyan G, Roberts A J, Hedlund P B. The 5-HT(7) receptor as a mediator and modulator of antidepressant-like behavior. Behav Brain Res 2010; 209: 99-108.
17. Hedlund P B, Huitron-Resendiz S, Henriksen S J, Sutcliffe J G. 5-HT7 receptor inhibition and inactivation induce antidepressantlike behavior and sleep pattern. Biol Psychiatry 2005; 58: 831-837.
18. Wesolowska A, Nikiforuk A, Stachowicz K, Tatarczynska E. Effect of the selective 5-HT7 receptor antagonist SB 269970 in animal models of anxiety and depression. Neuropharmacology 2006; 51: 578-586.
19. Mullins U L, Gianutsos G, Eison A S. Effects of antidepressants on 5-HT7 receptor regulation in the rat hypothalamus. Neuropsychopharmacology 1999; 21: 352-367.
20. Sleight A J, Carob C, Petit N et al. Identification of 5-hydroxytryptamine7 receptor binding sites in rat hypothalamus: sensitivity to chronic antidepressant treatment. Mol Pharmacol 1995; 47: 99-103.
21. Roth B L, Craigo S C, Choudhary M S et al. Binding of typical and atypical antipsychotic agents to 5-hydroxytryptamine-6 and 5-hydroxytryptamine-7 receptors. J Pharmacol Exp Ther 1994; 268: 1403-1410.
22. Monsma F J, Jr., Shen Y, Ward R P et al. Cloning and expression of a novel serotonin receptor with high affinity for tricyclic psychotropic drugs. Mol Pharmacol 1993; 43: 320-327.
23. Abbas A I, Hedlund P B, Huang X P et al. Amisulpride is a potent 5-HT7 antagonist: relevance for antidepressant actions in vivo. Psychopharmacology (Berl) 2009; 205: 119-128.
24. Ishibashi T, Horisawa T, Tokuda K et al. Pharmacological profile of lurasidone, a novel antipsychotic agent with potent 5-hydroxytryptamine 7 (5-HT7) and 5-HT1A receptor activity. J Pharmacol Exp Ther 2010; 334: 171-181.
25. Martinsson L, Wei Y, Xu D et al. Long-term lithium treatment in bipolar disorder is associated with longer leukocyte telomeres. Transl Psychiatry 2013; 3: e261.
26. Licht R W. Lithium: still a major option in the management of bipolar disorder. CNS Neurosci Ther 2012; 18: 219-226.
27. Post R M, Leverich G S, Nolen W A et al. A re-evaluation of the role of antidepressants in the treatment of bipolar depression: data from the Stanley Foundation Bipolar Network. Bipolar Disord 2003; 5: 396-406.
28. Gijsman H J, Geddes J R, Rendell J M et al. Antidepressants for bipolar depression: a systematic review of randomized, controlled trials. Am J Psychiatry 2004; 161: 1537-1547.
29. Vazquez G H, Tondo L, Undurraga J, Baldessarini R J. Overview of antidepressant treatment of bipolar depression. Int J Neuropsychopharmacol 2013; 16: 1673-1685.
30. Uher R, Perroud N, Ng M Y et al. Genome-wide pharmacogenetics of antidepressant response in the GENDEP project. Am J Psychiatry 2010; 167: 555-564.
31. Ising M, Lucae S, Binder E B et al. A genomewide association study points to multiple loci that predict antidepressant drug treatment outcome in depression. Arch Gen Psychiatry 2009; 66: 966-975.
32. Garriock H A, Kraft J B, Shyn S I et al. A genomewide association study of citalopram response in major depressive disorder. Biol Psychiatry 2010; 67: 133-138.
33. Nurnberger J I, Jr., Blehar M C, Kaufmann C A et al. Diagnostic interview for genetic studies. Rationale, unique features, and training. NIMH Genetics Initiative. Arch Gen Psychiatry 1994; 51: 849-859; discussion 863-844.
34. Andrews S. FastQC: A quality control tool for high throughput sequence data. 2015.
35. Li H, Handsaker B, Wysoker A et al. The Sequence Alignment/Map format and SAMtools. Bioinformatics 2009; 25: 2078-2079.
36. Bansal V. A statistical method for the detection of variants from next-generation resequencing of DNA pools. Bioinformatics 2010; 26: i318-324.
37. Wang K, Li M, Hakonarson H. ANNOVAR: functional annotation of genetic variants from high-throughput sequencing data. Nucleic Acids Res 2010; 38: e164.
38. Hennings J M, Owashi T, Binder E B et al. Clinical characteristics and treatment outcome in a representative sample of depressed inpatients—findings from the Munich Antidepressant Response Signature (MARS) project. J Psychiatr Res 2009; 43: 215-229.
39. Hamilton M. A rating scale for depression. J Neurol Neurosurg Psychiatry 1960; 23: 56-62.
40. Uher R, Huezo-Diaz P, Perroud N et al. Genetic predictors of response to antidepressants in the GENDEP project. Pharmacogenomics J 2009; 9: 225-233.
41. Montgomery S A, Asberg M. A new depression scale designed to be sensitive to change. Br J Psychiatry 1979; 134: 382-389.
42. Hamilton M. Development of a rating scale for primary depressive illness. Br J Soc Clin Psychol 1967; 6: 278-296.
43. Beck A T, Ward C H, Mendelson M et al. An inventory for measuring depression. Arch Gen Psychiatry 1961; 4: 561-571.
44. Uher R, Farmer A, Maier W et al. Measuring depression: comparison and integration of three scales in the GENDEP study. Psychol Med 2008; 38: 289-300.
45. Wei Y B, Martinsson L, Liu J J et al. hTERT genetic variation in depression. J Affect Disord 2016; 189: 62-69.
46. Purcell S, Neale B, Todd-Brown K et al. PLINK: a tool set for whole-genome association and population-based linkage analyses. Am J Hum Genet 2007; 81: 559-575.
47. Mink S, Haenig B, Klempnauer K H. Interaction and functional collaboration of p300 and C/EBPbeta. Mol Cell Biol 1997; 17: 6609-6617.

48. Stein B, Yang M X. Repression of the interleukin-6 promoter by estrogen receptor is mediated by NF-kappa B and C/EBP beta. Mol Cell Biol 1995; 15: 4971-4979.
49. Lovenberg T W, Baron B M, de Lecea L et al. A novel adenylyl cyclase-activating serotonin receptor (5-HT7) implicated in the regulation of mammalian circadian rhythms. Neuron 1993; 11: 449-458.
50. Thomas D R, Melotto S, Massagrande M et al. SB-656104-A, a novel selective 5-HT7 receptor antagonist, modulates REM sleep in rats. Br J Pharmacol 2003; 139: 705-714.
51. Roberts A J, Hedlund P B. The 5-HT(7) receptor in learning and memory. Hippocampus 2012; 22: 762-771.
52. Findlay L J, El-Mallakh P, El-Mallakh R S. Management of bipolar I depression: clinical utility of lurasidone. Ther Clin Risk Manag 2015; 11: 75-81.
53. Martenyi F, Dossenbach M, Mraz K, Metcalfe S. Gender differences in the efficacy of fluoxetine and maprotiline in depressed patients: a double-blind trial of antidepressants with serotonergic or norepinephrinergic reuptake inhibition profile. Eur Neuropsychopharmacol 2001; 11: 227-232.
54. Keers R, Aitchison K J. Gender differences in antidepressant drug response. Int Rev Psychiatry 2010; 22: 485-500.
55. Diflorio A, Jones I. Is sex important? Gender differences in bipolar disorder. Int Rev Psychiatry 2010; 22: 437-452.
56. Estrada-Camarena E, Lopez-Rubalcava C, Vega-Rivera N et al. Antidepressant effects of estrogens: a basic approximation. Behav Pharmacol 2010; 21: 451-464.
57. Speranza L, Chambery A, Di Domenico M et al. The serotonin receptor 7 promotes neurite outgrowth via ERK and Cdk5 signaling pathways. Neuropharmacology 2013; 67: 155-167.
58. Speranza L, Labus J, Volpicelli F et al. Serotonin 5-HT7 receptor increases the density of dendritic spines and facilitates synaptogenesis in forebrain neurons. J Neurochem 2017; 141: 647-661.
59. Ciranna L, Catania M V. 5-HT7 receptors as modulators of neuronal excitability, synaptic transmission and plasticity: physiological role and possible implications in autism spectrum disorders. Front Cell Neurosci 2014; 8: 250.

EMBODIMENTS

Embodiment 1

A method of determining whether a neuroactive drug is suitable for treating a subject undergoing treatment for a neuropsychiatric disorder comprising determining a rs7905446 single nucleotide polymorphism (SNP) in the subject, wherein the presence of a TT genotype indicates that a selective serotonin reuptake inhibitor (SSRI) or noradrenergic reuptake inhibitor (NARI) is unsuitable for treating the subject; and, wherein the presence of a GG or GT genotype indicates that a SSRI or noradrenergic reuptake inhibitor (NARI) is suitable for treating the subject.

Embodiment 2

The method of Embodiment 1, wherein the SSRI is paroxetine, fluoxetine, citalopram or escitalopram.

Embodiment 3

The method of Embodiment 1, wherein the NARI is desipramine, nortyptiline, bupropion, mirtazapine, maprotiline or atomoxetine.

Embodiment 4

The method of Embodiment 1, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 5

The method of Embodiment 1, wherein the method comprises obtaining a biological sample from the subject for determining the rs7905446 single nucleotide polymorphism (SNP) in the subject.

Embodiment 6

The method of Embodiment 5, wherein the biological sample comprises blood, cheek swab or orally obtained cells, or skin biopsy.

Embodiment 7

The method of Embodiment 1, the method further comprising detecting a rs6583737, rs12254390, or rs111631884 single nucleotide polymorphism (SNP).

Embodiment 8

The method of Embodiment 1, wherein the neuropsychiatric disorder comprises bipolar disorder, unipolar depression, obsessive-compulsive disorder, eating disorder, or migraine.

Embodiment 9

A method of determining whether a neuroactive drug is suitable for treating a subject undergoing treatment for a neuropsychiatric disorder comprising determining a rs7905446 single nucleotide polymorphism (SNP) in the subject, wherein the presence of a TT genotype indicates that amitriptyline, amoxapine, amisulpride, clozapine, aripiprazole, lurasidone, risperidone or perospirone is unsuitable for treating the subject, and wherein the presence of the GG or GT genotype indicates that amitriptyline, amoxapine, amisulpride, clozapine, aripiprazole, lurasidone, risperidone or perospirone is suitable for treating the subject.

Embodiment 10

The method of Embodiment 9, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 11

The method of Embodiment 9, wherein the method comprises obtaining a biological sample from the subject for determining the rs7905446 single nucleotide polymorphism (SNP) in the subject.

Embodiment 12

The method of Embodiment 11, wherein the biological sample comprises blood, cheek swab, orally obtained cells, or skin biopsy.

Embodiment 13

The method of Embodiment 9, the method further comprising detecting a rs6583737, rs12254390, or rs111631884 single nucleotide polymorphism (SNP).

Embodiment 14

The method of Embodiment 9, wherein the neuropsychiatric disorder comprises bipolar disorder, unipolar depression, obsessive-compulsive disorder, eating disorder, or migraine.

Embodiment 15

A method of treating a subject for a neuropsychiatric disorder comprising: determining a rs7905446 single nucleotide polymorphism (SNP) in the subject; and administering an effective amount of a SSRI or NARI to the subject if a GG or GT genotype is present; or, administering an effective amount of a neuroactive compound other than SSRI or NARI to the subject if a TT genotype is present.

Embodiment 16

The method of Embodiment 15, wherein the SSRI is paroxetine, fluoxetine, citalopram or escitalopram.

Embodiment 17

The method of Embodiment 15, wherein the NARI is desipramine, nortyptiline, bupropion, mirtazapine, maprotiline or atomoxetine.

Embodiment 18

The method of Embodiment 15, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 19

The method of Embodiment 15, wherein the method comprises obtaining a biological sample from the subject for determining the rs7905446 single nucleotide polymorphism (SNP) in the subject.

Embodiment 20

The method of Embodiment 19, wherein the biological sample comprises blood, cheek swab, orally obtained cells, or skin biopsy.

Embodiment 21

The method of Embodiment 15, the method further comprising detecting a rs6583737, rs12254390, or rs111631884 single nucleotide polymorphism (SNP).

Embodiment 22

The method of Embodiment 15, wherein the neuropsychiatric disorder comprises bipolar disorder, unipolar depression, obsessive-compulsive disorder, eating disorder, or migraine.

Embodiment 23

A method of treating a subject for a neuropsychiatric disorder comprising: determining a rs7905446 single nucleotide polymorphism (SNP) in the subject; and administering an effective amount of amitriptyline, amoxapine, amisulpride, clozapine, aripiprazole, lurasidone, risperidone or perospirone to the subject if a GG or GT genotype is present; or, administering an effective amount of a neuroactive compound other than amitriptyline, amoxapine, amisulpride, clozapine, aripiprazole, lurasidone, risperidone or perospirone to the subject if a TT genotype is present.

Embodiment 24

The method of Embodiment 23, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 25

The method of Embodiment 23, wherein the method comprises obtaining a biological sample from the subject for determining the rs7905446 single nucleotide polymorphism (SNP) in the subject.

Embodiment 26

The method of Embodiment 25, wherein the biological sample comprises blood, cheek swab, orally obtained cells, or skin biopsy.

Embodiment 27

The method of Embodiment 23, the method further comprising detecting a rs6583737, rs12254390, or rs111631884 single nucleotide polymorphism (SNP).

Embodiment 28

The method of Embodiment 23, wherein the neuropsychiatric disorder comprises bipolar disorder, unipolar depression, obsessive-compulsive disorder, eating disorder, or migraine.

Embodiment 29

A method of treating a subject for a neuropsychiatric disorder, said subject undergoing treatment with a SSRI or NARI, comprising: determining a rs7905446 single nucleotide polymorphism (SNP) in the subject; and continuing administration of an effective amount of a SSRI or NARI to the subject if a GG or GT genotype is present; or, discontinuing administration of a SSRI or NARI to the subject if a TT genotype is present and administering an effective amount of a neuroactive compound other than a SSRI or NARI.

Embodiment 30

The method of Embodiment 29, wherein the SSRI is paroxetine, fluoxetine, citalopram or escitalopram.

Embodiment 31

The method of Embodiment 29, wherein the NARI is desipramine, nortyptiline, bupropion, mirtazapine, maprotiline or atomoxetine.

Embodiment 32

The method of Embodiment 29, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 33

The method of Embodiment 29, wherein the method comprises obtaining a biological sample from the subject for determining the rs7905446 single nucleotide polymorphism (SNP) in the subject.

Embodiment 34

The method of Embodiment 33, wherein the biological sample comprises blood, cheek swab, orally obtained cells, or skin biopsy.

Embodiment 35

The method of Embodiment 29, the method further comprising detecting a rs6583737, rs12254390, or rs111631884 single nucleotide polymorphism (SNP).

Embodiment 36

The method of Embodiment 29, wherein the neuropsychiatric disorder comprises bipolar disorder, unipolar depression, obsessive-compulsive disorder, eating disorder, or migraine.

Embodiment 37

A method of treating a subject for a neuropsychiatric disorder comprising: determining the rs7905446 single nucleotide polymorphism (SNP) in the subject; and continuing administration of amitriptyline, amoxapine, amisulpride, clozapine, aripiprazole, lurasidone, risperidone or perospirone to the subject if a GG or GT genotype is present; or, discontinuing administration of amitriptyline, amoxapine, amisulpride, clozapine, aripiprazole, lurasidone, risperidone or perospirone to the subject if a TT genotype is present and administering an effective amount of a neuroactive compound other than amitriptyline, amoxapine, amisulpride, clozapine, aripiprazole, lurasidone, risperidone or perospirone.

Embodiment 38

The method of Embodiment 37, wherein the method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 39

The method of Embodiment 37, wherein the method comprises obtaining a biological sample from the subject for determining the rs7905446 single nucleotide polymorphism (SNP) in the subject.

Embodiment 40

The method of Embodiment 39, wherein the biological sample comprises blood, cheek swab, orally obtained cells, or skin biopsy.

Embodiment 41

The method of Embodiment 37, the method further comprising detecting a rs6583737, rs12254390, or rs111631884 single nucleotide polymorphism (SNP).

Embodiment 42

The method of Embodiment 37, wherein the neuropsychiatric disorder comprises bipolar disorder, unipolar depression, obsessive-compulsive disorder, eating disorder, or migraine.

Embodiment 43

A method of detecting a single nucleotide polymorphism (SNP) in a subject, said method comprising detecting in a biological sample from said subject the presence of a rs7905446 single nucleotide polymorphism (SNP).

Embodiment 44

The method of Embodiment 43, wherein said subject has or is at risk of having a neuropsychiatric disorder.

Embodiment 45

The method of Embodiment 44, wherein said neuropsychiatric disorder comprises bipolar disorder, unipolar depression, obsessive-compulsive disorder, eating disorder, or migraine.

Embodiment 46

The method of Embodiment 43, wherein said method comprises detecting the rs7905446 single nucleotide polymorphism (SNP) by 5' exonuclease polymerase chain reaction, DNA sequencing, restriction fragment length polymorphism, chip hybridization or single base extension assay.

Embodiment 47

The method of Embodiment 43, wherein the method comprises obtaining a biological sample from the subject for determining the rs7905446 single nucleotide polymorphism (SNP) in said subject.

Embodiment 48

The method of Embodiment 47, wherein the biological sample comprises blood, cheek swab, orally obtained cells, or skin biopsy.

Embodiment 49

The method of Embodiment 43, the method further comprising detecting a rs6583737, rs12254390, or rs111631884 single nucleotide polymorphism (SNP).

Embodiment 50

A kit for predicting the suitability of a neuroactive compound in a subject with a neuropsychiatric disorder comprising at least one nucleic acid probe or primer for detecting a rs7905446 single nucleotide polymorphism (SNP).

---

What is claimed is:

1. A method of treating a subject for a neuropsychiatric disorder comprising:
   determining a rs7905446 single nucleotide polymorphism (SNP) genotype in the subject; and
   administering an effective amount of a selective serotonin reuptake inhibitor (SSRI), serotonin and norepinephrine reuptake inhibitor (SNRI) or noradrenergic reuptake inhibitor (NARI) to the subject if a GG or GT genotype is present; or,
   administering an effective amount of a neuroactive compound other than SSRI, SNRI or NARI to the subject if a TT genotype is present.

2. The method of claim 1, wherein the SSRI is paroxetine, fluoxetine, citalopram or escitalopram.

3. The method of claim 1, wherein the NARI is desipramine, nortyptiline, bupropion, mirtazapine, maprotiline or atomoxetine.

4. The method of claim 1, wherein the method comprises determining the rs7905446 single nucleotide polymorphism (SNP) genotype by 5' exonuclease polymerase chain reaction, DNA sequencing, restriction fragment length polymorphism, chip hybridization or single base extension assay.

5. The method of claim 1, wherein the method comprises obtaining a biological sample from the subject for determining the rs7905446 single nucleotide polymorphism (SNP) genotype in the subject.

6. The method of claim 1, the method further comprising determining a rs6583737, rs12254390, or rs111631884 single nucleotide polymorphism (SNP) genotype.

7. The method of claim 1, wherein the neuropsychiatric disorder comprises bipolar disorder, unipolar depression, obsessive-compulsive disorder, eating disorder, or migraine.

8. A method of assaying single nucleotide polymorphism (SNP) genotypes in a subject, wherein said subject has or is at risk of having a neuropsychiatric disorder, said method consisting of assaying in a biological sample from said subject (a) the genotype of a rs7905446 single nucleotide polymorphism (SNP) and (b) the genotype of one or more of a rs6583737, rs12254390, rs111631884, rs1935346, rs4262637, or rs7912164 single nucleotide polymorphism (SNP).

9. The method of claim 8, wherein said neuropsychiatric disorder comprises bipolar disorder, unipolar depression, obsessive-compulsive disorder, eating disorder, or migraine.

10. The method of claim 8, wherein said assaying the rs7905446 single nucleotide polymorphism (SNP) is by 5' exonuclease polymerase chain reaction, DNA sequencing, restriction fragment length polymorphism, chip hybridization or single base extension assay.

* * * * *